United States Patent
Yoon et al.

(10) Patent No.: US 12,180,177 B2
(45) Date of Patent: Dec. 31, 2024

(54) COMPOUND AND ORGANIC LIGHT EMITTING DIODE COMPRISING SAME

(71) Applicant: LG CHEM, LTD., Seoul (KR)

(72) Inventors: Hongsik Yoon, Daejeon (KR); Wanpyo Hong, Daejeon (KR); Jin Joo Kim, Daejeon (KR); Dong Hoon Lee, Daejeon (KR); Su Jin Han, Daejeon (KR); Seulchan Park, Daejeon (KR)

(73) Assignee: LG Chem, Ltd., Seoul (KR)

( * ) Notice: Subject to any disclaimer, the term of this patent is extended or adjusted under 35 U.S.C. 154(b) by 1013 days.

(21) Appl. No.: 17/056,729

(22) PCT Filed: Jul. 9, 2019

(86) PCT No.: PCT/KR2019/008421
§ 371 (c)(1),
(2) Date: Nov. 18, 2020

(87) PCT Pub. No.: WO2020/013574
PCT Pub. Date: Jan. 16, 2020

(65) Prior Publication Data
US 2021/0198232 A1 Jul. 1, 2021

(30) Foreign Application Priority Data
Jul. 9, 2018 (KR) .................. 10-2018-0079362

(51) Int. Cl.
| | |
|---|---|
| *C07D 333/76* | (2006.01) |
| *H10K 50/15* | (2023.01) |
| *H10K 50/16* | (2023.01) |
| *H10K 50/17* | (2023.01) |
| *H10K 50/18* | (2023.01) |
| *H10K 85/60* | (2023.01) |

(52) U.S. Cl.
CPC ......... *C07D 333/76* (2013.01); *H10K 85/654* (2023.02); *H10K 85/6572* (2023.02); *H10K 85/6574* (2023.02); *H10K 85/6576* (2023.02); *H10K 50/15* (2023.02); *H10K 50/16* (2023.02); *H10K 50/171* (2023.02); *H10K 50/18* (2023.02)

(58) Field of Classification Search
CPC ............. H10K 85/654; H10K 85/6574; H10K 85/6576; H10K 85/6572; H10K 50/16; H10K 50/18; H10K 50/171; H10K 50/15; C07D 307/91; C07D 333/76
See application file for complete search history.

(56) References Cited

U.S. PATENT DOCUMENTS

| | | | |
|---|---|---|---|
| 2002/0121860 A1* | 9/2002 | Seo | H10K 77/10 313/506 |
| 2014/0158992 A1 | 6/2014 | Xia et al. | |
| 2017/0054087 A1 | 2/2017 | Zeng et al. | |
| 2017/0194574 A1 | 7/2017 | Ishidai et al. | |
| 2017/0213988 A1 | 7/2017 | Park et al. | |
| 2018/0037546 A1* | 2/2018 | Sugino | C07D 209/82 |
| 2018/0072945 A1 | 3/2018 | Otsu et al. | |
| 2018/0194992 A1 | 7/2018 | Aou et al. | |
| 2019/0386226 A1 | 12/2019 | Parham et al. | |
| 2019/0393430 A1 | 12/2019 | Park et al. | |

FOREIGN PATENT DOCUMENTS

| | | |
|---|---|---|
| CN | 107922827 A | 4/2018 |
| KR | 10-2016-0142909 A | 12/2016 |
| KR | 10-2017-0013152 A | 2/2017 |
| KR | 10-2017-0057660 A | 5/2017 |
| KR | 10-2017-0082447 A | 7/2017 |
| KR | 10-2018-0071621 A | 7/2017 |
| KR | 10-2017-0102000 A | 9/2017 |
| KR | 10-2017-0131537 A | 11/2017 |
| WO | 2015-051869 A1 | 4/2015 |

* cited by examiner

*Primary Examiner* — Dylan C Kershner
(74) *Attorney, Agent, or Firm* — Bryan Cave Leighton Paisner LLP

(57) ABSTRACT

A compound of Chemical Formula 1, and an organic light emitting device including the same.

[Chemical Formula 1]

10 Claims, 2 Drawing Sheets

|   |
|---|
| 4 |
| 9 |
| 8 |
| 3 |
| 6-2 |
| 6-1 |
| 5 |
| 2 |
| 1 |

FIG. 3

COMPOUND AND ORGANIC LIGHT EMITTING DIODE COMPRISING SAME

This application is a National Stage of International Application No. PCT/KR2019/008421, filed on Jul. 9, 2019, which claims priority to and the benefits of Korean Patent Application No. 10-2018-0079362, filed with the Korean Intellectual Property Office on Jul. 9, 2018, the entire contents of which are incorporated herein by reference.

TECHNICAL FIELD

The present specification relates to a compound, and an organic light emitting device including the same.

BACKGROUND ART

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection or the like may also be used as a material of the organic thin film.

Development of an organic thin film material has been continuously required for enhancing performance, lifetime or efficiency of an organic light emitting device.

DISCLOSURE

Technical Problem

The present specification is directed to providing a compound, and an organic light emitting device including the same.

Technical Solution

One embodiment of the present specification provides a compound of the following Chemical Formula 1.

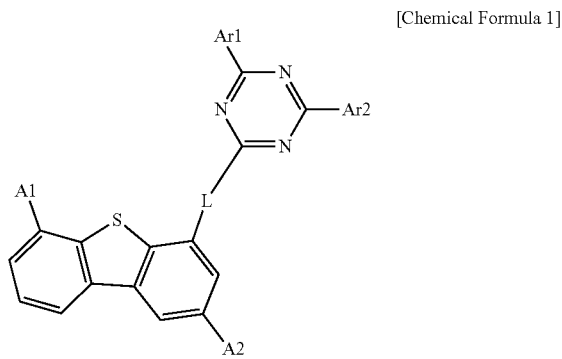

[Chemical Formula 1]

In Chemical Formula 1,

A1 and A2 are the same as or different from each other, and each independently a substituted or unsubstituted carbazole group, L is a direct bond; or a substituted or unsubstituted arylene group, Ar1 and Ar2 are the same as or different from each other, and each independently a substituted or unsubstituted aryl group; a substituted or unsubstituted heterocyclic group; or a substituted or unsubstituted silyl group.

Another embodiment of the present application provides an organic light emitting device including a first electrode; a second electrode provided opposite to the first electrode; and one or more organic material layers provided between the first electrode and the second electrode, wherein one or more layers of the organic material layers include the compound described above.

Advantageous Effects

A compound according to one embodiment of the present application is used in an organic light emitting device, and capable of increasing luminance, increasing a lifetime, lowering a driving voltage and enhancing light efficiency of the organic light emitting device, and enhancing device lifetime properties by thermal stability of the compound.

The compound of Chemical Formula 1 according to one embodiment of the present application enhances durability of a material by blocking an active site of the S atom when a carbazole group bonds to a number 2 position (A2) of dibenzothiophene, and enhances durability of a material by shielding surroundings of the S atom when a carbazole group bonds to a number 6 position (A1) thereof. Accordingly, an effect of long lifetime is obtained when using the compound according to Chemical Formula 1 in an organic light emitting device.

DESCRIPTION OF DRAWINGS

FIGS. 1 to 3 illustrate examples of an organic light emitting device.

REFERENCE NUMERAL

Figure 1:
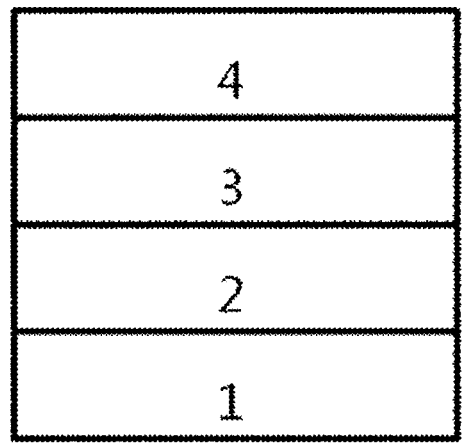

1: Substrate
2: Anode
3: Light Emitting Layer
4: Cathode
5: Hole Injection Layer
6: Hole Transfer Layer
6-1: First Hole Transfer Layer
6-2: Second Hole Transfer Layer
7: Electron Blocking Layer
8: Hole Blocking Layer
9: Electron Injection and Transfer Layer

DETAILED DESCRIPTION

Hereinafter, the present specification will be described in more detail.

One embodiment of the present specification provides a compound of Chemical Formula 1.

The compound of Chemical Formula 1 enhances durability by bonding two carbazole groups to number 2 (A2) and number 6 (A1) positions of dibenzothiophene, and enhances electron mobility while shielding surroundings of the S atom by bonding a triazine group to a number 4 position thereof.

Examples of substituents in the present specification will be described below, however, the substituents are not limited thereto.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the term "substituted or unsubstituted" means being substituted with one, two or more substituents selected from the group consisting of deuterium; a halogen group; a nitrile group; an alkyl group; a cycloalkyl group; a silyl group; an alkoxy group; an aryl group; and a heterocyclic group, or being substituted with a substituent linking two or more substituents of the substituents illustrated above, or having no substituents. For example, a "substituent linking two or more substituents" may include a biphenyl group. In other words, a biphenyl group may be an aryl group, or may be interpreted as a substituent linking two phenyl groups.

In the present specification, examples of the halogen group may include fluorine, chlorine, bromine or iodine.

In the present specification, the alkyl group may be linear or branched, and although not particularly limited thereto, the number of carbon atoms is preferably from 1 to 50. Specific examples thereof may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethylpropyl, isohexyl, 2-methylpentyl, 4-methylhexyl, 5-methylhexyl and the like, but are not limited thereto.

In the present specification, the cycloalkyl group is not particularly limited, but preferably has 3 to 30 carbon atoms. Specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the alkoxy group may be linear, branched or cyclic. The number of carbon atoms of the alkoxy group is not particularly limited, but is preferably from 1 to 30. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, when the aryl group is a monocyclic aryl group, the number of carbon atoms is not particularly limited, but is preferably from 6 to 30. Specific examples of the monocyclic aryl group may include a phenyl group, a biphenyl group, a terphenyl group and the like, but are not limited thereto.

When the aryl group is a polycyclic aryl group, the number of carbon atoms is not particularly limited, but is preferably from 10 to 24. Specific examples of the polycyclic aryl group may include a naphthyl group, an anthracene group, a phenanthrene group, a pyrenyl group, a perylenyl group, a chrysene group, a fluorene group and the like, but are not limited thereto.

In the present specification, the heteroaryl group is a group including one or more atoms that are not carbon, that is, heteroatoms, and specifically, the heteroatom may include one or more atoms selected from the group consisting of O, N, Se, Si, S and the like. The number of carbon atoms of the heteroaryl group is not particularly limited, but is preferably from 2 to 60 or 2 to 30. Examples of the heteroaryl group may include a thiophene group, a furan group, a pyrrole group, an imidazolyl group, a thiazolyl group, an oxazolyl group, an oxadiazolyl group, a triazolyl group, a pyridyl group, a bipyridyl group, a pyrimidyl group, a triazinyl group, an acridyl group, a pyridazinyl group, a pyrazinyl group, a quinolinyl group, a quinazolinyl group, a quinoxalinyl group, a phthalazinyl group, a pyridopyrimidinyl group, a pyridopyrazinyl group, a pyrazinopyrazinyl group, an isoquinolinyl group, an indole group, a carbazolyl group, a benzoxazolyl group, a benzimidazolyl group, a benzothiazolyl group, a benzocarbazolyl group, a dibenzocarbazolyl group, a benzothiophene group, a dibenzothiophene group, a benzofuran group, a dibenzofuran group, a benzosilole group, a dibenzosilole group, a phenanthrolinyl group, an isoxazolyl group, a thiadiazolyl group, a phenothiazinyl group, a phenoxazine group, fused structures thereof, and the like, but are not limited thereto.

In the present specification, the arylene group means the aryl group having two bonding sites, that is, a divalent group. Descriptions on the aryl group provided above may be applied thereto except for those that are each a divalent.

In the present specification, the arylsilyl group means a silyl group substituted with an aryl group, and the aryl in the arylsilyl group has the same examples as the aryl group described above.

In the present specification, the alkylsilyl group means a silyl group substituted with an alkyl group, and the alkyl group has the same examples as the alkyl group described above.

In one embodiment of the present specification, the compound of Chemical Formula 1 is of the following Chemical Formula 2.

[Chemical Formula 2]

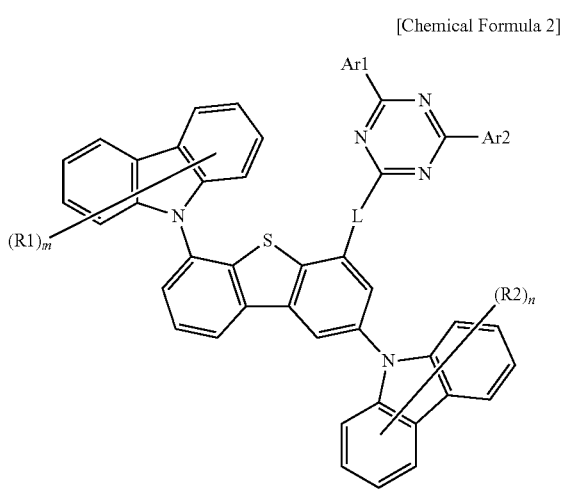

In Chemical Formula 2,

L, Ar1 and Ar2 have the same definitions as in Chemical Formula 1,

R1 and R2 are the same as or different from each other, and each independently hydrogen; deuterium; a halogen group; a nitrile group; a nitro group; a substituted or unsubstituted alkyl group; a substituted or unsubstituted cycloalkyl group; a substituted or unsubstituted arylsilyl group; a substituted or unsubstituted alkylsilyl group; a substituted or unsubstituted alkoxy group; a substituted or unsubstituted aryl group; or a substituted or unsubstituted heterocyclic group, m and n are each an integer of 0 to 8, when m is 2 or greater, R1s are the same as or different from each other, and when n is 2 or greater, R2s are the same as or different from each other.

In one embodiment of the present specification, L is a direct bond; or a substituted or unsubstituted phenylene group.

In one embodiment of the present specification, L is a direct bond; or a phenylene group.

In one embodiment of the present specification, L is a direct bond; a para-phenylene group; or a meta-phenylene group.

In one embodiment of the present specification, Ar1 and Ar2 are the same as or different from each other, and each independently a substituted or unsubstituted phenyl group; a substituted or unsubstituted biphenyl group; a substituted or unsubstituted dibenzothiophene group; a substituted or unsubstituted dibenzofuran group; or a substituted or unsubstituted benzothiazole group.

In one embodiment of the present specification, Ar1 and Ar2 are the same as or different from each other, and each independently a phenyl group unsubstituted or substituted with a nitrile group; a biphenyl group unsubstituted or substituted with a nitrile group; a dibenzothiophene group unsubstituted or substituted with a nitrile group; a dibenzofuran group unsubstituted or substituted with a nitrile group; or a benzothiazole group unsubstituted or substituted with a nitrile group.

In one embodiment of the present specification, Ar1 and Ar2 are the same as or different from each other, and each independently a phenyl group unsubstituted or substituted with a nitrile group; a biphenyl group; a dibenzothiophene group; a dibenzofuran group; or a benzothiazole group.

In one embodiment of the present specification, the compound of Chemical Formula 1 is selected from among the following structural formulae.

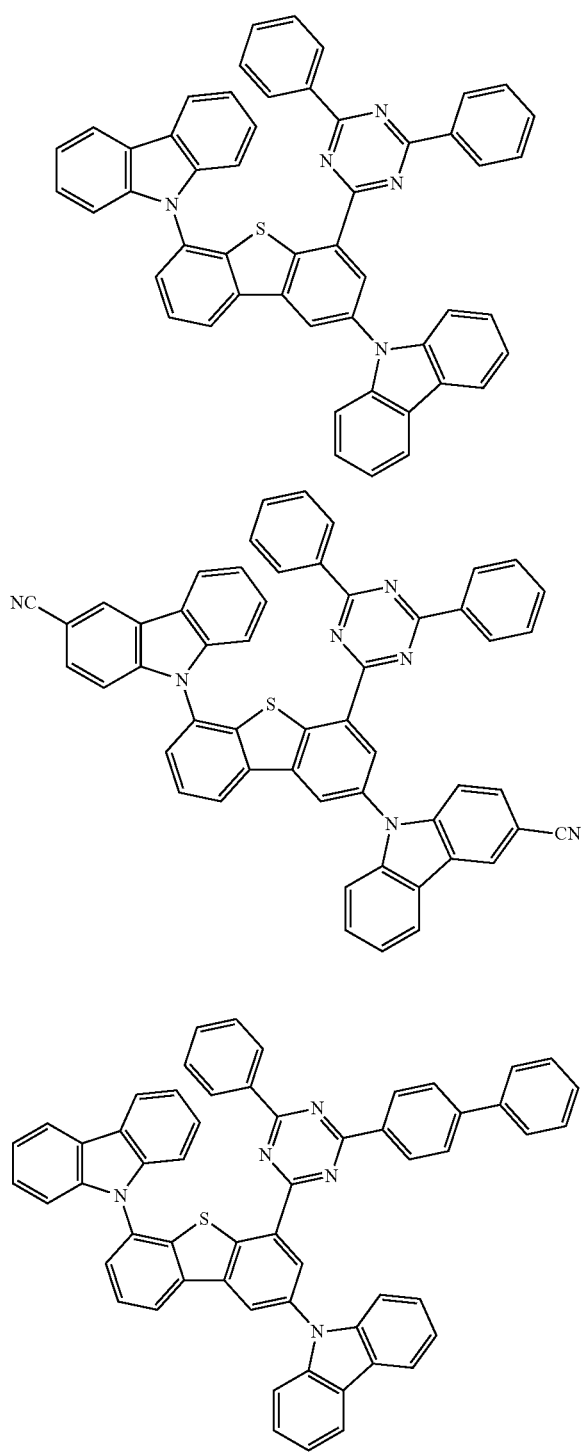

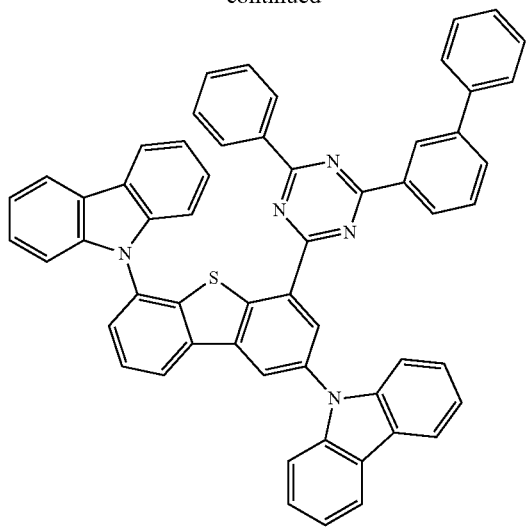
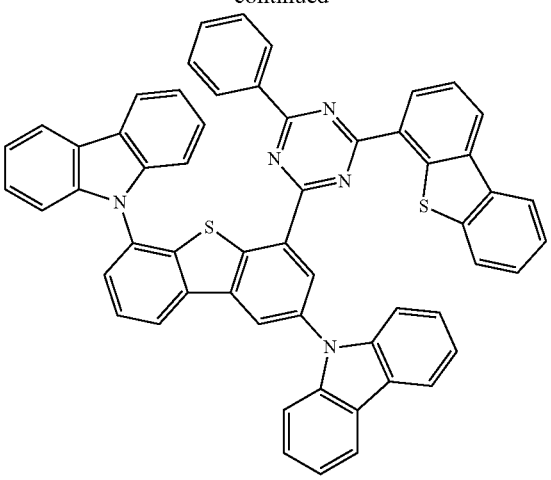
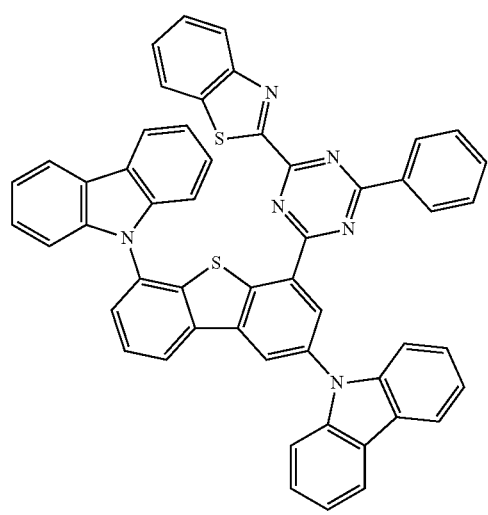
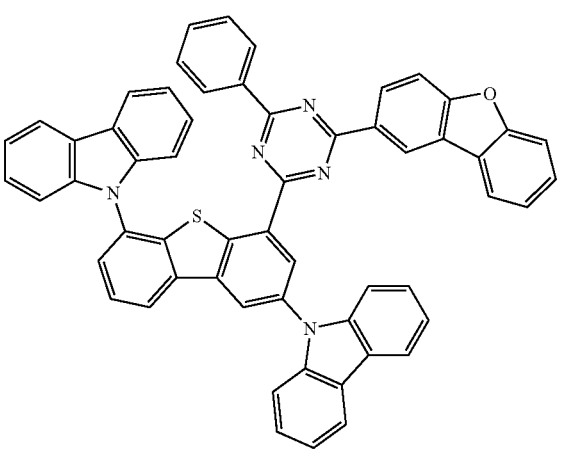
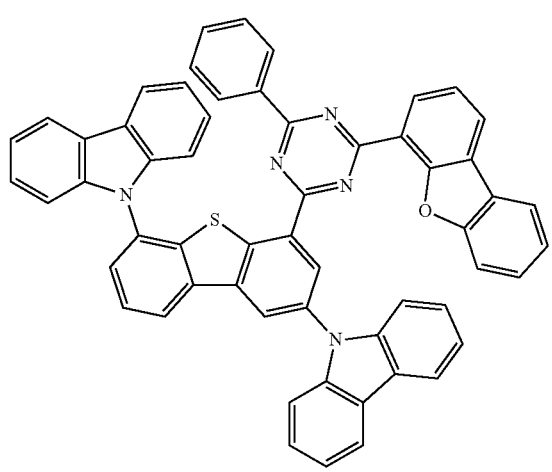

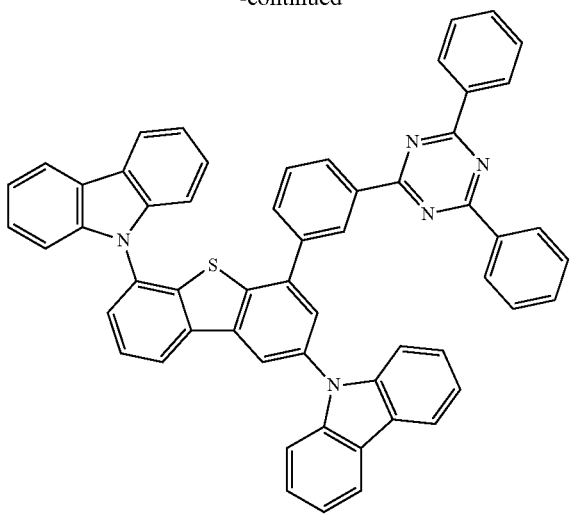

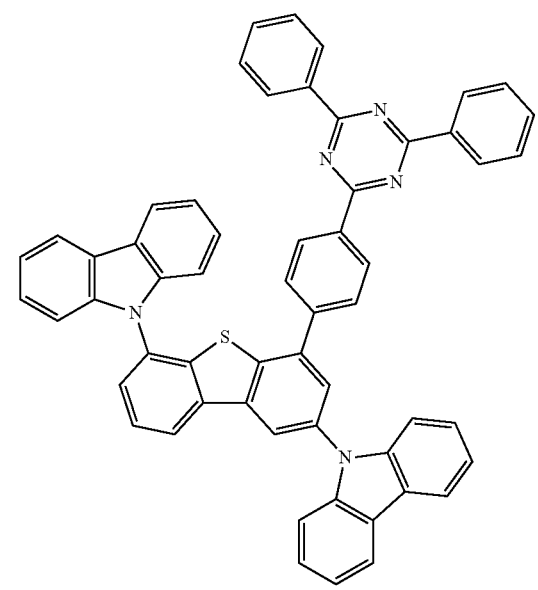

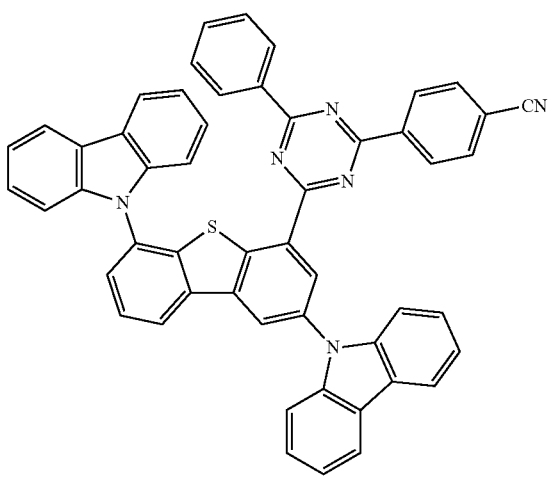

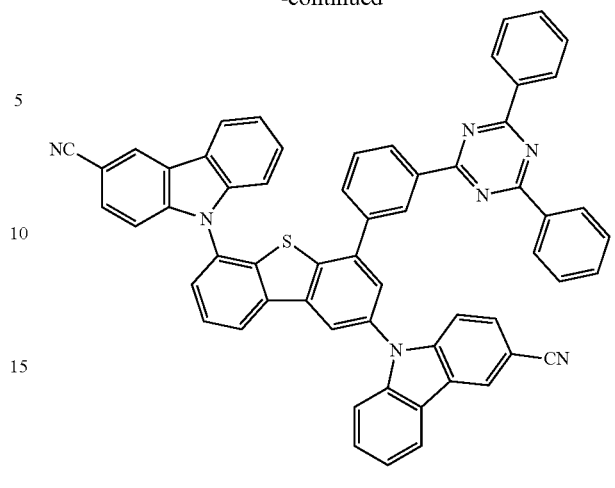

The compound according to one embodiment of the present application may be prepared using a preparation method to describe below.

For example, the compound of Chemical Formula 1 may have its core structure prepared as in the following Reaction Formula 1. Substituents may bond using methods known in the art, and types, positions or the number of the substituents may vary depending on technologies known in the art.

[Reaction Formula 1]

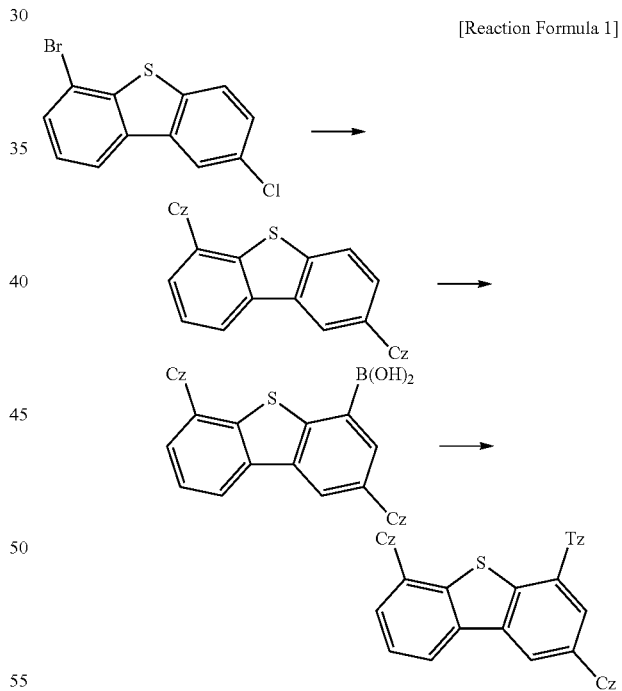

After introducing a carbazole-based group (Cz) to 6-bromo-2-chlorodibenzo[b,d]thiophene using an amination reaction, boronic acid is introduced to the number 4 position using n-butyl lithium, and by finally introducing a triazine group (Tz) thereto through a Suzuki reaction, the compound of Chemical Formula 1 may be prepared.

In one embodiment of the present specification, the compound of Chemical Formula 1 has a glass transition temperature of 120° C. or higher.

In one embodiment of the present specification, the compound of Chemical Formula 1 has a glass transition temperature of higher than or equal to 120° C. and lower than or equal to 200° C., and when satisfying the above-mentioned range, high purity is obtained using a sublimation purification method, and when manufacturing an organic light emitting device, no contamination is caused to a film-forming apparatus for deposition or the organic light emitting device.

As for the glass transition temperature according to the present specification, calories depending on an increase and decrease in the temperature are measured through a differential scanning calorimetry (DSC) measurement device.

Another embodiment of the present specification provides an organic light emitting device including the compound described above.

One embodiment of the present application provides an organic light emitting device including a first electrode; a second electrode provided opposite to the first electrode; and one or more organic material layers provided between the first electrode and the second electrode, wherein one or more layers of the organic material layers include the compound.

In the present specification, a description of one member being placed "on" another member includes not only a case of the one member adjoining the another member but a case of still another member being present between the two members.

In the present specification, a description of a certain part "including" certain constituents means capable of further including other constituents, and does not exclude other constituents unless particularly stated on the contrary.

The organic material layer of the organic light emitting device of the present application may be formed in a single layer structure, but may be formed in a multilayer structure in which two or more organic material layers are laminated. For example, as a representative example of the organic light emitting device of the present disclosure, the organic light emitting device may have a structure including a hole injection layer, a hole transfer layer, a light emitting layer, an electron transfer layer, an electron injection layer and the like as the organic material layer. However, the structure of the organic light emitting device is not limited thereto, and may include a smaller number of organic material layers.

In one embodiment of the present application, the organic material layer includes a light emitting layer, and the light emitting layer includes the compound.

In one embodiment of the present application, the organic material layer includes a light emitting layer, and the light emitting layer includes the compound as a host.

In one embodiment of the present application, the organic material layer includes a light emitting layer, the light emitting layer includes the compound as a host, and further includes another host material.

In one embodiment of the present application, the organic material layer includes a light emitting layer, the light emitting layer includes the compound as a host, and further includes an auxiliary host material.

In one embodiment of the present application, the organic material layer includes a light emitting layer, the light emitting layer includes the compound as a host and further includes another host material, and includes the compound and the another host material in a weight ratio of 10:1 to 1:2.

In one embodiment of the present application, the organic material layer includes a light emitting layer, the light emitting layer includes the compound as a host and further includes another host material, and includes the compound and the another host material in a weight ratio of 3:1 to 1:1.

According to one embodiment of the present specification, the light emitting layer may include a compound having a triplet energy level of 2.1 eV or higher, and may preferably include a compound having a triplet energy level of higher than or equal to 2.1 eV and lower than or equal to 3.0 eV, higher than or equal to 2.3 eV and lower than or equal to 3.0 eV, and higher than or equal to 2.3 eV and lower than or equal to 2.9 eV. When including a compound satisfying the above-mentioned energy level in the light emitting layer, electrons are readily injected increasing an exciton formation rate, which leads to an advantage of increasing light emission efficiency.

According to one embodiment of the present specification, the light emitting layer may include a compound having a difference between a singlet energy level and a triplet energy level of higher than or equal to 0 eV and lower than or equal to 0.3 eV, and may preferably include a compound having the difference of higher than or equal to 0 eV and lower than or equal to 0.25 eV. When including a compound having a difference between a singlet energy level and a triplet energy level satisfying the above-mentioned range in the light emitting layer, a ratio and a speed of excitons produced at the triplet energy level moving to the singlet energy level by reverse intersystem crossing (RISC) increase reducing the time of the excitons staying at the triplet energy, and advantages of increasing efficiency and lifetime of the organic light emitting device are obtained.

In the present specification, the triplet energy may be measured using a spectrometer capable of measuring fluorescence and phosphorescence, and as for the measurement condition, a solution is prepared in a concentration of $10^{-6}$ M with toluene or THF as a solvent in a cryogenic state obtained using liquid nitrogen, and from a spectrum emitting light by irradiating a light source in an absorption wavelength range of the material on the solution, singlet light emission is excluded, and the spectrum emitting light at the triplet is analyzed and identified. When electrons are reversed from the light source, the time for the electrons staying at the triplet is much longer than the time staying at the singlet, and two components may be separated in a cryogenic state.

In the present specification, the singlet energy is measured using a fluorescent device, and unlike the method of measuring the triplet energy described above, a light source is irradiated at room temperature.

According to another embodiment, the organic material layer includes a light emitting layer, the light emitting layer includes the compound, and may further include a host and a fluorescent dopant.

In a general organic light emitting device, excitons produced at singlet and triplet are produced in a ratio of 25:75 (singlet:triplet), and depending on the light emission type resulting from the exciton migration, light emission may be divided into fluorescent light emission, phosphorescent light emission and heat-activated delayed fluorescent light emission. The phosphorescent light emission means light emission obtained by excitons in a triplet excited state migrating to a ground state, the fluorescent light emission means light emission obtained by excitons in a singlet excited state migrating to a ground state, and the heat-activated delayed fluorescent light emission means producing fluorescent light emission by inducing reverse intersystem crossing from a triplet excited state to a singlet excited state, and excitons in the singlet excited state migrating to a ground state.

By the light emitting layer of the present disclosure including a compound having delayed fluorescent properties, an organic light emitting device having high efficiency may be generally obtained by excitons in a triplet excited state reverse intersystem crossing to a singlet excited state, and transferring the energy to a dopant.

The organic light emitting device of the present disclosure has delayed fluorescent properties and phosphorescent light emission properties.

According to one embodiment of the present specification, the another host material is a carbazole-based compound.

In one embodiment of the present application, the organic material layer includes a light emitting layer, and the light emitting layer may further include a dopant.

In one embodiment of the present application, the organic material layer includes a light emitting layer, the light emitting layer further includes a dopant, and the dopant is a metal complex.

In one embodiment of the present application, the organic material layer includes a light emitting layer, the light emitting layer further includes a dopant, and the dopant is an iridium-based complex.

In one embodiment of the present application, the organic material layer includes a light emitting layer, the light emitting layer further includes a dopant, and the dopant is an iridium-based dopant.

In one embodiment of the present application, the organic material layer includes a light emitting layer, and the light emitting layer includes the compound and the dopant in a content ratio of 1:1 to 100:1.

In one embodiment of the present application, the organic material layer includes a hole injection layer or a hole transfer layer, and the hole injection layer or the hole transfer layer includes the compound.

In one embodiment of the present application, the organic material layer includes a hole injection layer, a hole transfer layer, or a hole injection and transfer layer, and the hole injection layer, the hole transfer layer, or the hole injection and transfer layer includes the compound.

In one embodiment of the present application, the organic material layer includes two or more hole transfer layers.

In one embodiment of the present application, the organic material layer includes an electron blocking layer. In one embodiment of the present application, the organic material layer includes an electron transfer layer or an electron injection layer, and the electron transfer layer or the electron injection layer includes the compound.

In one embodiment of the present application, the organic material layer includes an electron injection layer, an electron transfer layer, or an electron injection and transfer layer, and the electron injection layer, the electron transfer layer, or the electron injection and transfer layer includes the compound.

In one embodiment of the present application, the organic material layer includes a hole blocking layer.

In one embodiment of the present application, the organic light emitting device includes a first electrode; a second electrode provided opposite to the first electrode; a light emitting layer provided between the first electrode and the second electrode; and two or more organic material layers provided between the light emitting layer and the first electrode, or between the light emitting layer and the second electrode, wherein at least one of the two or more organic material layers includes the compound.

In another embodiment, the organic light emitting device may be an organic light emitting device having a structure in which an anode, one or more organic material layers and a cathode are consecutively laminated on a substrate (normal type).

In another embodiment, the organic light emitting device may be an organic light emitting device having a structure in a reverse direction in which a cathode, one or more organic material layers and an anode are consecutively laminated on a substrate (inverted type).

For example, a structure of the organic light emitting device according to one embodiment of the present application is illustrated in FIG. 1.

FIG. 1 illustrates a structure of the organic light emitting device in which a substrate (1), an anode (2), a light emitting layer (3) and a cathode (4) are consecutively laminated. In such a structure, the compound may be included in the light emitting layer (3).

Figure 2:
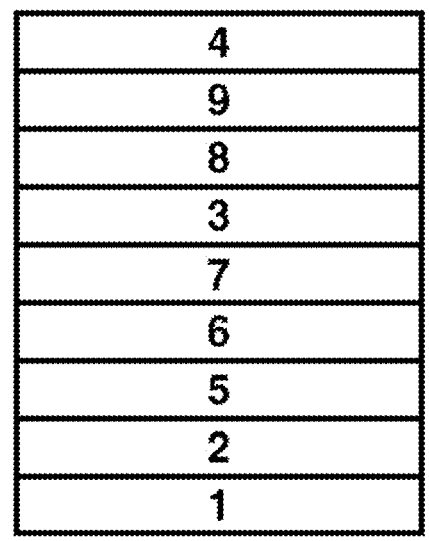

FIG. 2 illustrates a structure of the organic light emitting device in which a substrate (1), an anode (2), a hole injection layer (5), a hole transfer layer (6), an electron blocking layer (7), a light emitting layer (3), a hole blocking layer (8), an electron injection and transfer layer (9) and a cathode (4) are consecutively laminated. In such a structure, the compound may be included in the light emitting layer (3).

Figure 3:
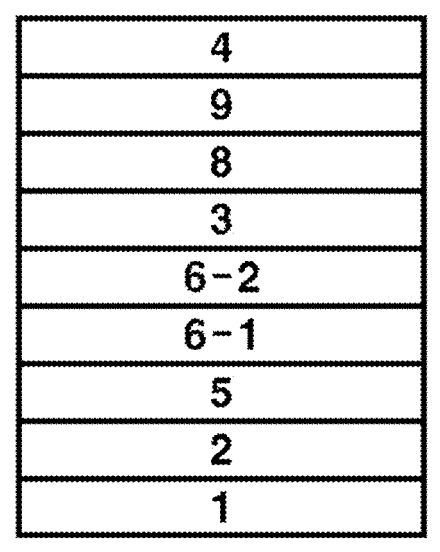

FIG. 3 illustrates a structure of the organic light emitting device in which a substrate (1), an anode (2), a hole injection layer (5), a first hole transfer layer (6-1), a second hole transfer layer (6-2), a light emitting layer (3), a hole blocking layer (8), an electron injection and transfer layer (9) and a cathode (4) are consecutively laminated. In such a structure, the compound may be included in the light emitting layer (3).

The organic light emitting device of the present application may be manufactured using materials and methods known in the art, except that one or more layers of the organic material layers include the compound of the present application, that is, the above-described compound.

When the organic light emitting device includes a plurality of organic material layers, the organic material layers may be formed with materials the same as or different from each other.

For example, the organic light emitting device of the present application may be manufactured by consecutively laminating a first electrode, an organic material layer and a second electrode on a substrate. Herein, the organic light emitting device may be manufactured by forming an anode on a substrate by depositing a metal, a metal oxide having conductivity, or an alloy thereof using a physical vapor deposition (PVD) method such as sputtering or e-beam evaporation, and forming an organic material layer including a hole injection layer, a hole transfer layer, a light emitting layer and an electron transfer layer thereon, and then depositing a material capable of being used as a cathode thereon. In addition to such a method, the organic light emitting device may also be manufactured by consecutively depositing a cathode material, an organic material layer and an anode material on a substrate.

In addition, the compound of Chemical Formula 1 may be formed into an organic material layer using a solution coating method as well as a vacuum deposition method when manufacturing the organic light emitting device. Herein, the solution coating method means spin coating, dip coating, doctor blading, inkjet printing, screen printing, a spray method, roll coating and the like, but is not limited thereto.

In addition to such as method, the organic light emitting device may also be manufactured by consecutively laminating a cathode material, an organic material layer and an anode material on a substrate (International Patent Application Laid-Open Publication No. 2003/012890). However, the manufacturing method is not limited thereto.

In one embodiment of the present application, the first electrode is an anode, and the second electrode is a cathode.

In another embodiment, the first electrode is a cathode, and the second electrode is an anode.

As the anode material, materials having large work function are normally preferred so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as $ZnO:Al$ or $SnO_2:Sb$; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as $LiF/Al$ or $LiO_2/Al$, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition thereto, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto. The hole injection layer may have a thickness of 1 nm to 150 nm. The hole injection layer having a thickness of 1 nm or greater has an advantage of preventing decline in the hole injection properties, and the thickness being 150 nm or less has an advantage of preventing an increase in the driving voltage to enhance hole migration caused from the hole injection layer being too thick.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suitable. Specific examples thereof include arylamine-based organic materials, conductive polymers, block copolymers having conjugated parts and non-conjugated parts together, and the like, but are not limited thereto.

An electron blocking layer may be provided between the hole transfer layer and a light emitting layer. As the electron blocking layer, materials known in the art may be used. The light emitting layer may emit red, green or blue light, and may be formed with a phosphorescent material or a fluorescent material. The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes ($Alq_3$); carbazole-based compounds; dimerized styryl compounds; BAlq; 10-hydroxybenzo quinoline-metal compounds; benzoxazole-, benzothiazole- and benzimidazole-based compounds; poly (p-phenylenevinylene) (PPV)-based polymers; spiro compounds; polyfluorene, rubrene, and the like, but are not limited thereto.

The light emitting layer may include a host material and a dopant material. The host material includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes compounds, dibenzofuran derivatives, ladder-type furan compounds, pyrimidine derivatives and the like, however, the material is not limited thereto.

When the light emitting layer emits red light, a phosphorescent material such as bis(1-phenylisoquinoline)acetylacetonate iridium (PIQIr(acac)), bis(1-phenylquinoline) acetylacetonate iridium (PQIr(acac)), tris(1-phenylquinoline) iridium (PQIr) or octaethylporphyrin platinum (PtOEP), or a fluorescent material such as tris(8-hydroxyquinolino)aluminum ($Alq_3$) may be used as a light emitting dopant, however, the light emitting dopant is not limited thereto. When the light emitting layer emits green light, a phosphorescent material such as fac tris(2-phenylpyridine)iridium ($Ir(ppy)_3$), or a fluorescent material such as tris(8-hydroxyquinolino)aluminum ($Alq_3$), an anthracene-based compound, a pyrene-based compound or a boron-based compound may be used as a light emitting dopant, however, the light emitting dopant is not limited thereto. When the light emitting layer emits blue light, a phosphorescent material such as $(4,6-F2ppy)_2Irpic$, or a fluorescent material such as spiro-DPVBi, spiro-6P, distyrylbenzene (DSB), distyrylarylene (DSA), a PFO-based polymer, a PPV-based polymer, an anthracene-based compound, a pyrene-based compound or a boron-based compound may be used as a light emitting dopant, however, the light emitting dopant is not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suitable. Specific examples thereof include Al complexes of 8-hydroxyquinoline; complexes including $Alq_3$; organic radical compounds; hydroxyflavon-metal complexes, and the like, but are not limited thereto. The electron transfer layer may be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato) (o-cresolato)gallium, bis(2-methyl-8-quinolinato) (1-naphtholato)aluminum, bis(2-methyl-8-quinolinato) (2-naphtholato)gallium and the like, but is not limited thereto.

The hole blocking layer is a layer blocking holes from reaching a cathode and may be generally formed under the same condition as the hole injection layer. Specifically, oxadiazole derivatives, triazole derivatives, phenanthroline derivatives, BCP, aluminum complexes and the like are included, however, the hole blocking layer is not limited thereto.

The organic light emitting device according to the present specification may be a top-emission type, a bottom-emission type or a dual-emission type depending on the materials used.

Methods for preparing the compound of Chemical Formula 1 and manufacturing an organic light emitting device including the same will be specifically described in the following examples. However, the following examples are for illustrative purposes only, and the scope of the present specification is not limited thereby.

PREPARATION EXAMPLE

Preparation Example 1-1: Synthesis of Compound 1-A

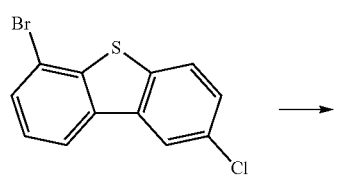

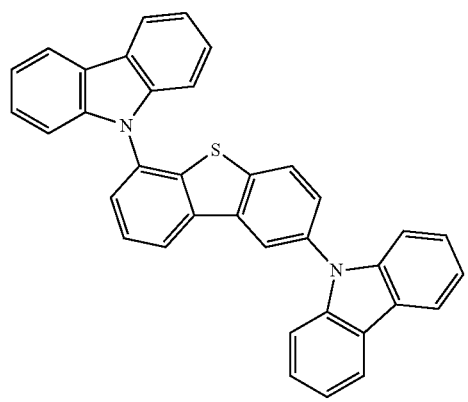

1-A

6-Bromo-2-chlorodibenzo[b,d]thiophene (30 g, 100.8 mmol), 9-H-carbazole (202 mmol), sodium-tert-butoxide (263 mmol) and toluene (300 mL) were mixed, and heated to 100° C. Tetrakistriphenylphosphine palladium (2 mmol) was added thereto, and the result was stirred for 3 hours under reflux. After the reaction, the reaction solution returned to room temperature was washed with water, and then the organic layer was recrystallized twice with chloroform and hexane to obtain Compound 1-A (45.6 g). (Yield 88%, MS[M+H]$^+$=515) Preparation Example 1-2: Synthesis of Compound 1-B

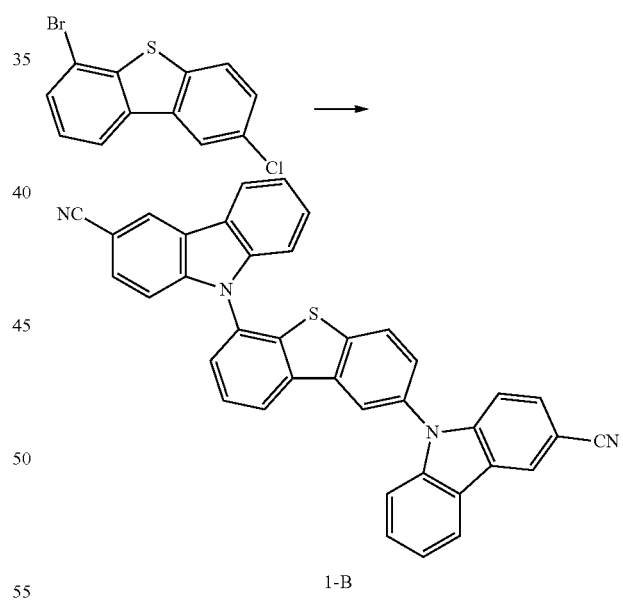

1-B

6-Bromo-2-chlorodibenzo[b,d]thiophene (30 g, 100.8 mmol), 9H-carbazole-3-carbonitrile (202 mmol), sodium-tert-butoxide (263 mmol) and toluene (300 mL) were mixed, and heated to 100° C. Tetrakistriphenylphosphine palladium (2 mmol) was added thereto, and the result was stirred for 3 hours under reflux. After the reaction, the reaction solution returned to room temperature was washed with water, and then the organic layer was recrystallized twice with chloroform and hexane to obtain Compound 1-B (48.4 g). (Yield 85%, MS[M+H]$^+$=565)

Preparation Example 2-1: Synthesis of Compound 2-A

Preparation Example 2-2: Synthesis of Compound 2-B

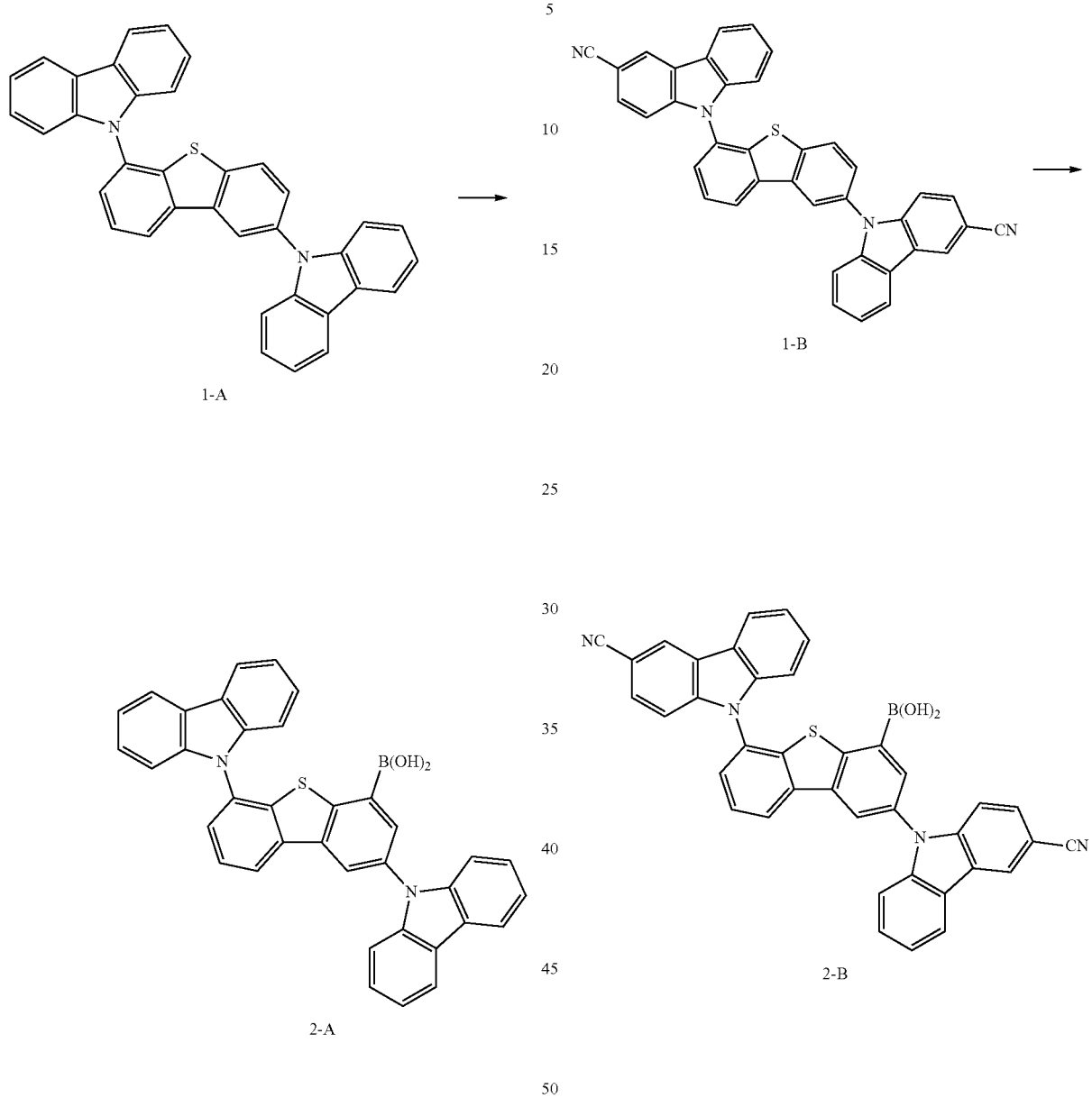

1-A (25.7 g, 50 mmol) and tetrahydrofuran (THF) (300 mL) were mixed and cooled to −78° C. After adding n-butyl lithium (55 mmol) thereto, the result was stirred for 2 hours at −78° C. Triisopropyl borate (60 mmol) was added thereto, the temperature was raised to room temperature, and the result was stirred for 2 hours. After the reaction, ethyl acetate (200 mL) and a saturated ammonium chloride solution (200 mL) were added to extract the organic layer, and the organic layer was recrystallized twice with chloroform and hexane to obtain Compound 2-A (22.6 g). (Yield 81%, MS[M+H]$^+$=559)

1-B (28.2 g, 50 mmol) and tetrahydrofuran (THF) (300 mL) were mixed and cooled to −78° C. After adding n-butyl lithium (55 mmol) thereto, the result was stirred for 2 hours at −78° C. Triisopropyl borate (60 mmol) was added thereto, the temperature was raised to room temperature, and the result was stirred for 2 hours. After the reaction, ethyl acetate (200 mL) and a saturated ammonium chloride solution (200 mL) were added to extract the organic layer, and the organic layer was recrystallized twice with chloroform and hexane to obtain Compound 2-B (23.4 g). (Yield 77%, MS[M+H]$^+$=609)

Preparation Example 3-1: Synthesis of Compound 1

Preparation Example 3-2: Synthesis of Compound 2

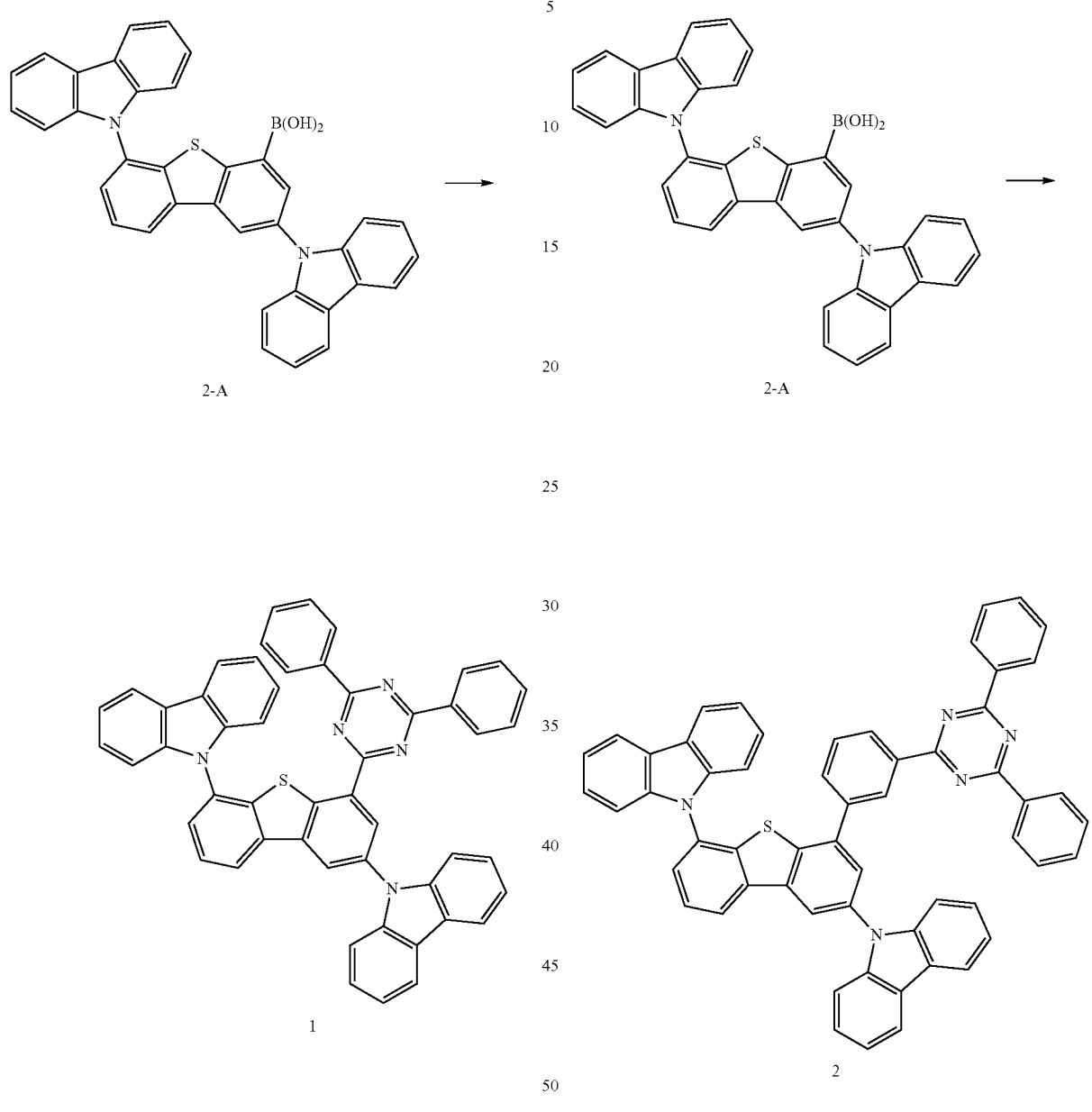

2-A (19.5 g, 35 mmol), 2-chloro-4,6-diphenyl-1,3,5-triazine (35 mmol), tetrahydrofuran (200 mL) and water (100 mL) were mixed and heated to 60° C. Potassium carbonate (105 mmol) and tetrakistriphenylphosphine palladium (0.7 mmol) were added thereto, and the result was stirred for 2 hours under reflux. After the reaction, the organic layer was extracted from the reaction solution returned to room temperature, and then recrystallized twice with chloroform and hexane to obtain Compound 1 (23.5 g). (Yield 90%, MS[M+H]$^+$=746)

2-A (19.5 g, 35 mmol), 2-(3-bromophenyl)-4,6-diphenyl-1,3,5-triazine (35 mmol), tetrahydrofuran (200 mL) and water (100 mL) were mixed and heated to 60°. Potassium carbonate (105 mmol) and tetrakistriphenylphosphine palladium (0.7 mmol) were added thereto, and the result was stirred for 2 hours under reflux. After the reaction, the organic layer was extracted from the reaction solution returned to room temperature, and then recrystallized twice with chloroform and hexane to obtain Compound 2 (24.7 g). (yield 86%, MS[M+H]$^+$=822)

Preparation Example 3-3: Synthesis of Compound 3

Preparation Example 3-4: Synthesis of Compound 4

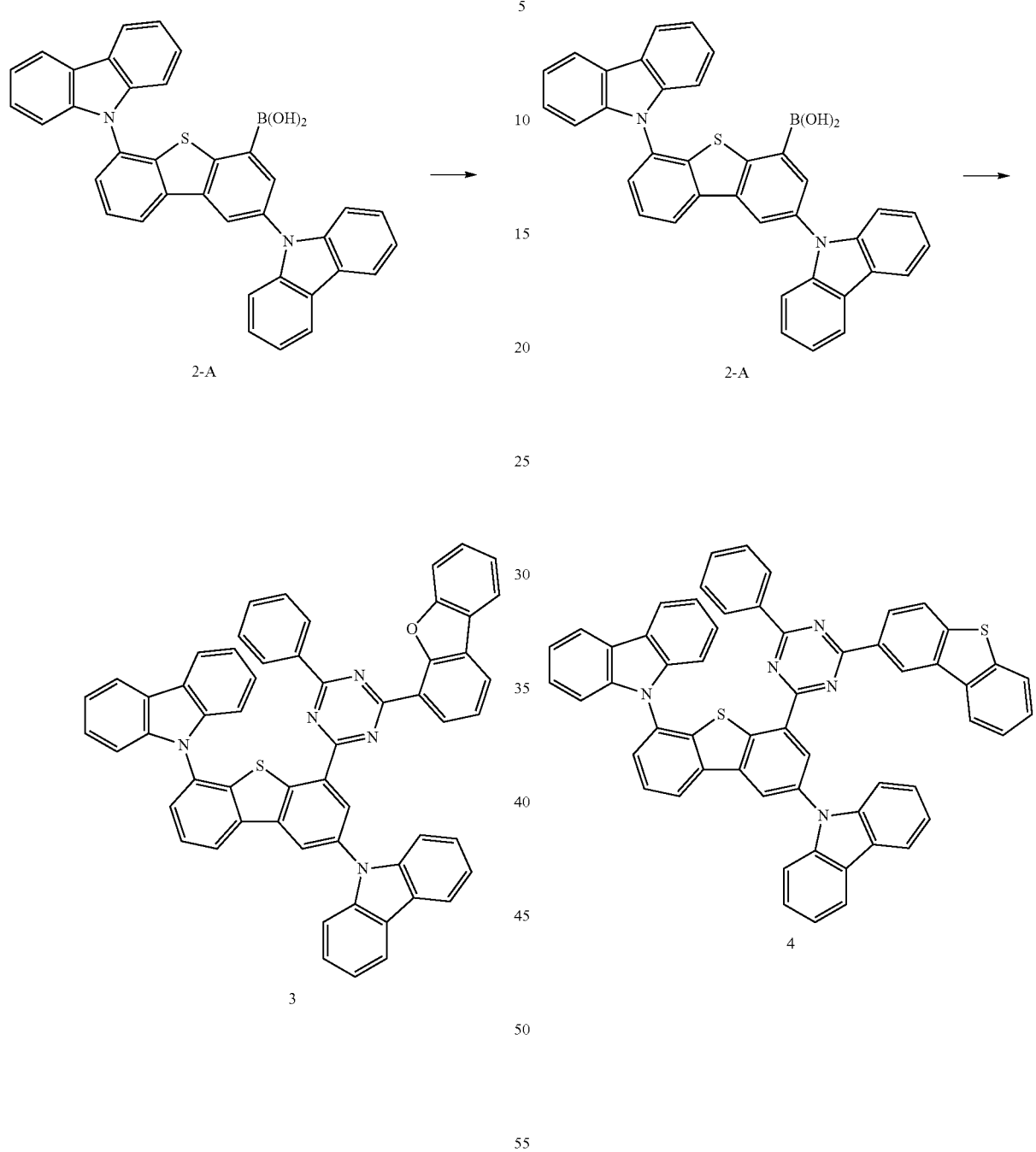

2-A (19.5 g, 35 mmol), 2-chloro-4-(dibenzo[b,d]furan-4-yl)-6-phenyl-1,3,5-triazine (35 mmol), tetrahydrofuran (200 mL) and water (100 mL) were mixed and heated to 60° C. Potassium carbonate (105 mmol) and tetrakistriphenylphosphine palladium (0.7 mmol) were added thereto, and the result was stirred for 2 hours under reflux. After the reaction, the organic layer was extracted from the reaction solution returned to room temperature, and then recrystallized twice with chloroform and hexane to obtain Compound 3 (24.3 g). (Yield 83%, MS[M+H]$^+$=836)

2-A (19.5 g, 35 mmol), 2-chloro-4-(dibenzo[b,d]thiophen-2-yl)-6-phenyl-1,3,5-triazine (35 mmol), tetrahydrofuran (200 mL) and water (100 mL) were mixed and heated to 60° C. Potassium carbonate (105 mmol) and tetrakistriphenylphosphine palladium (0.7 mmol) were added thereto, and the result was stirred for 2 hours under reflux. After the reaction, the organic layer was extracted from the reaction solution returned to room temperature, and then recrystallized twice with chloroform and hexane to obtain Compound 4 (23.8 g). (Yield 80%, MS[M+H]$^+$=852)

Preparation Example 3-5: Synthesis of Compound 5

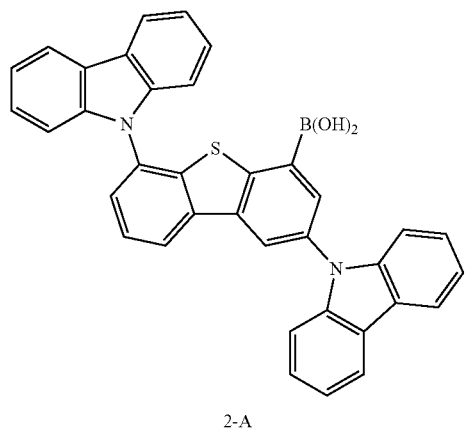

2-A

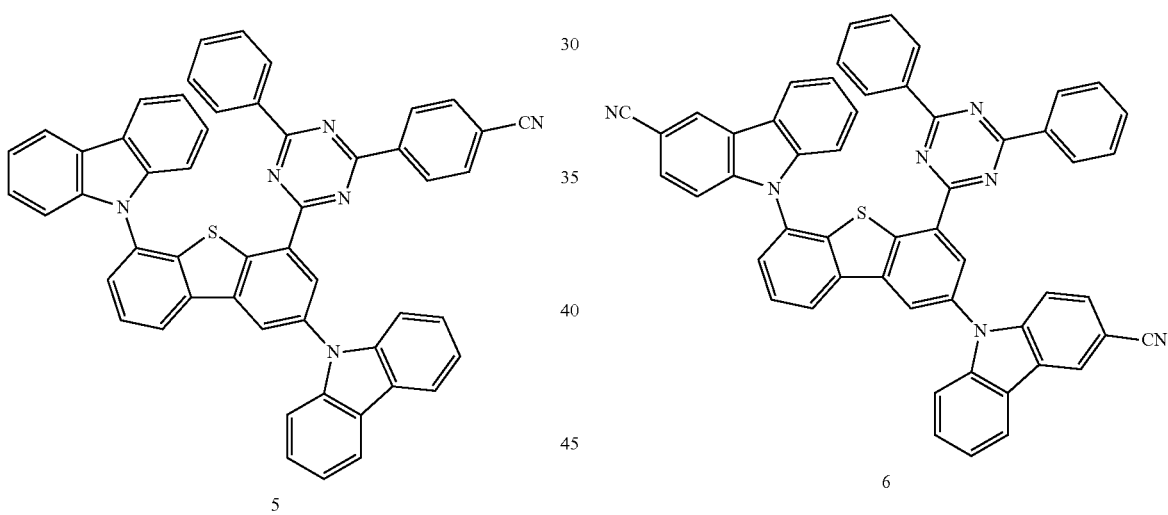

5

Preparation Example 3-6: Synthesis of Compound 6

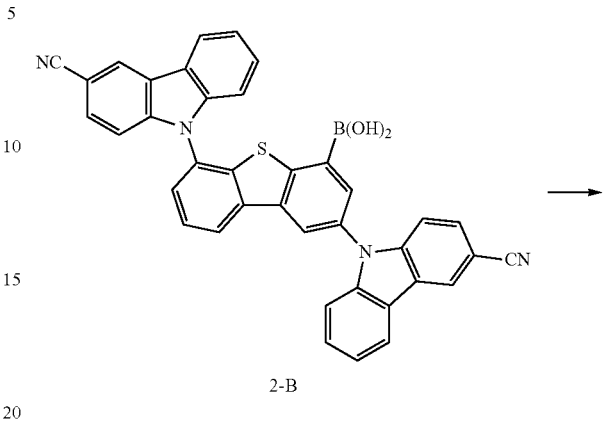

2-B

6

2-A (19.5 g, 35 mmol), 4-(4-chloro-6-phenyl-1,3,5-triazin-2-yl)benzonitrile (35 mmol), tetrahydrofuran (200 mL) and water (100 mL) were mixed and heated to 60° C. Potassium carbonate (105 mmol and tetrakistriphenylphosphine palladium (0.7 mmol) were added thereto, and the result was stirred for 2 hours under reflux. After the reaction, the organic layer was extracted from the reaction solution returned to room temperature, and then recrystallized twice with chloroform and hexane to obtain Compound 5 (21.8 g). (Yield 81%, MS[M+H]⁺=771)

2-B (21.3 g, 35 mmol), 2-chloro-4,6-diphenyl-1,3,5-triazine (35 mmol), tetrahydrofuran (200 mL) and water (100 mL) were mixed and heated to 60° C. Potassium carbonate (105 mmol) and tetrakistriphenylphosphine palladium (0.7 mmol) were added thereto, and the result was stirred for 2 hours under reflux. After the reaction, the organic layer was extracted from the reaction solution returned to room temperature, and then recrystallized twice with chloroform and hexane to obtain Compound 6 (20.6 g). (Yield 74%, MS [M+H]⁺=796)

Preparation Example 3-7: Synthesis of Compound 7

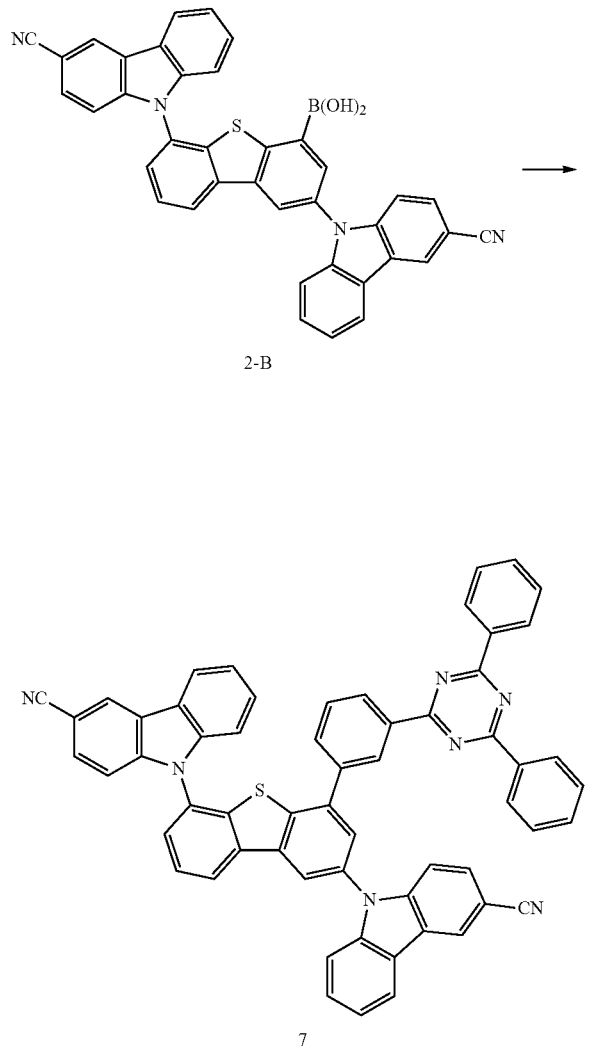

2-B (21.3 g, 35 mmol), 2-(3-bromophenyl)-4,6-diphenyl-1,3,5-triazine (35 mmol), tetrahydrofuran (200 mL) and water (100 mL) were mixed and heated to 60° C. Potassium carbonate (105 mmol) and tetrakistriphenylphosphine palladium (0.7 mmol) were added thereto, and the result was stirred for 2 hours under reflux. After the reaction, the organic layer was extracted from the reaction solution returned to room temperature, and then recrystallized twice with chloroform and hexane to obtain Compound 7 (21.6 g). (Yield 71%, MS[M+H]$^+$=872)

Through synthesis processes the same as the above-described reaction formula, materials in the specific examples were synthesized by diversely introducing substituents substituting the triazine group and substituents substituting the carbazole group.

EXAMPLE

Example 1-1

A glass substrate on which indium tin oxide (ITO) was coated as a thin film to a thickness of 100 nm was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor. On the transparent ITO electrode prepared as above, each thin film was laminated using a vacuum deposition method under a degree of vacuum of 5.0×10$^{-4}$ Pa. First, hexanitrile hexaazatriphenylene (HAT-CN) was thermal vacuum deposited to a thickness of 50 nm on the ITO to form a hole injection layer.

On the hole injection layer, a hole transfer layer (30 nm) was formed by vacuum depositing 4-4'-bis[N-(1-naphthyl)-N-phenylamino]biphenyl (NPB), a material transferring holes.

On the hole transfer layer, an electron blocking layer was formed by vacuum depositing N-([1,1'-bisphenyl]-4-yl)-N-(4-(11-([1,1'-biphenyl]-4-yl)-11H-benzo[a]carbazol-5-yl)phenyl)-[1,1'-biphenyl]-4-amine (EB1) (10 nm).

Subsequently, a light emitting layer (30 nm) was formed on the electron blocking layer by vacuum depositing Compound 1 and 4CzIPN in a weight ratio of 70:30. ($\Delta E_{ST}$ (difference between singlet energy and triplet energy) of the compound 4CzIPN was less than 0.2 eV.)

On the light emitting layer, a hole blocking layer was formed by vacuum depositing Compound HB1 to a film thickness of nm.

On the hole blocking layer, an electron injection and transfer layer was formed to a thickness of 30 nm by vacuum depositing Compound ET1 and Compound LiQ (lithium quinolate) in a weight ratio of 1:1. A cathode was formed on the electron injection and transfer layer by consecutively depositing lithium fluoride (LiF) to a thickness of 1.2 nm and aluminum to a thickness of 200 nm.

In the above-mentioned process, the deposition rates of the organic materials were maintained at 0.04 nm/sec to 0.07 nm/sec, the deposition rate of the lithium fluoride was maintained at 0.03 nm/sec, the deposition rate of the aluminum was maintained at 0.2 nm/sec, and the degree of vacuum during the deposition was maintained at 2×10$^{-7}$ torr to 5×10$^{-6}$ torr to manufacture an organic light emitting device.

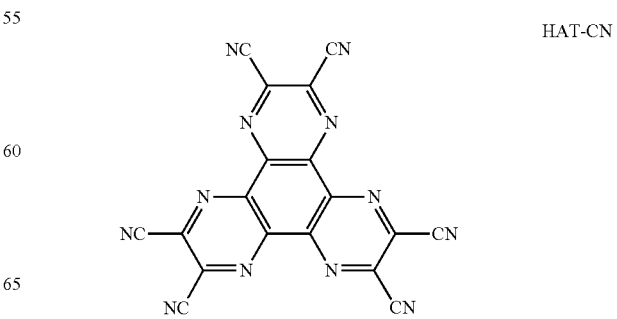

HAT-CN

NPB

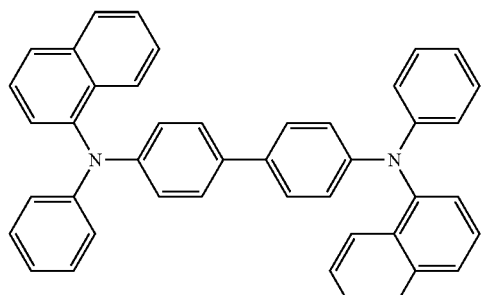

HB1

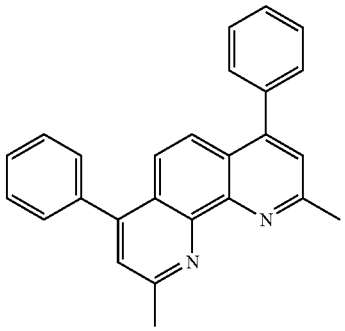

EB1

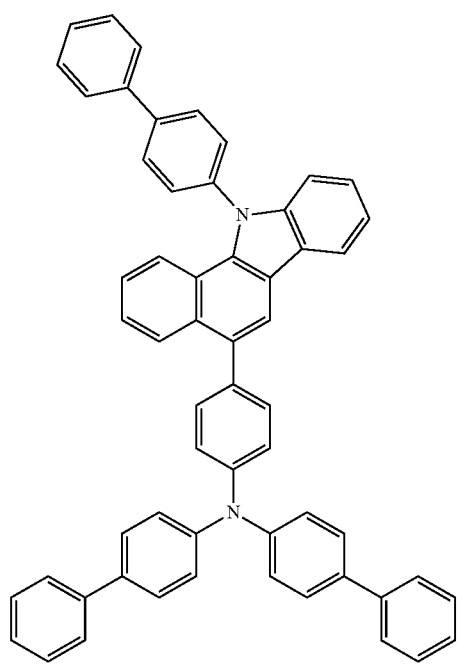

ET1

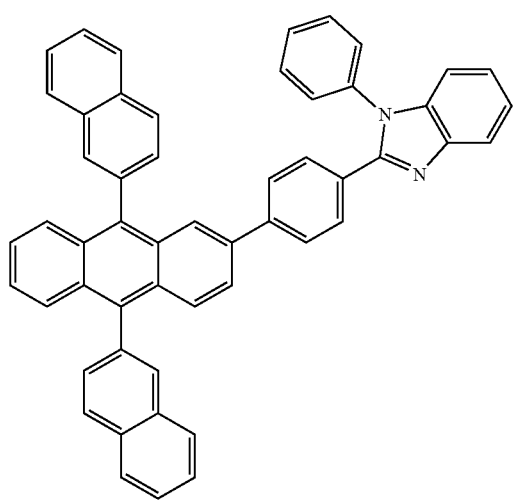

LiQ

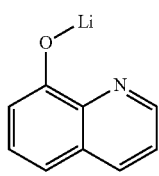

4CzIPN

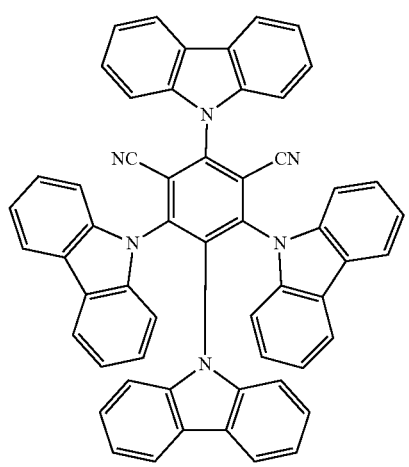

Examples 1-2 to 1-7

Organic light emitting devices were manufactured in the same manner as in Example 1-1 except that compounds of the following Table 1 were used instead of Compound 1.

Comparative Examples 1-1 to 1-6

Organic light emitting devices were manufactured in the same manner as in Example 1-1 except that compounds of the following Table 1 were used instead of Compound 1.

GH2
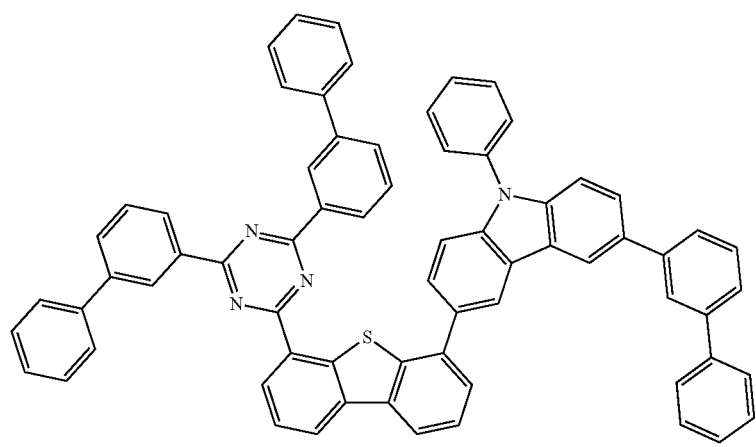
GH3
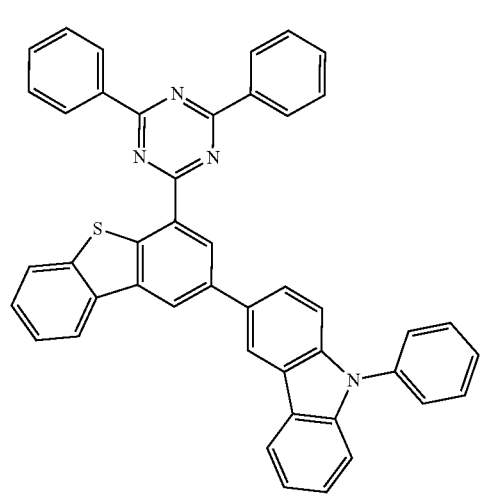
GH4
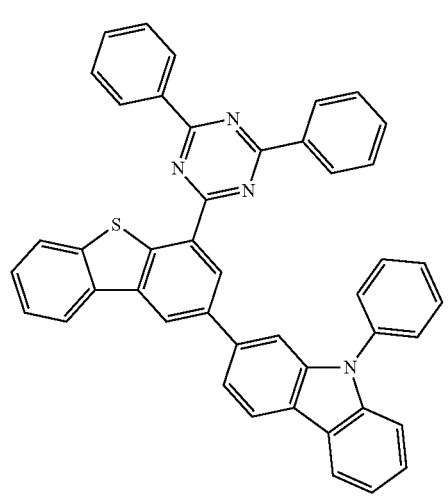

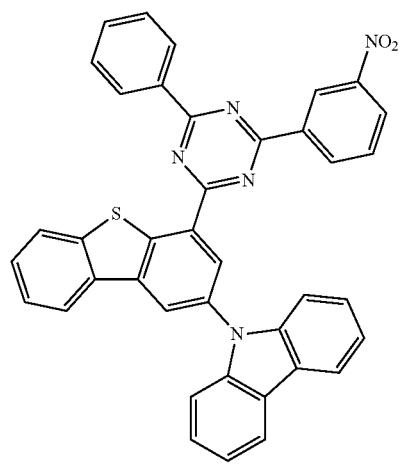
GH5
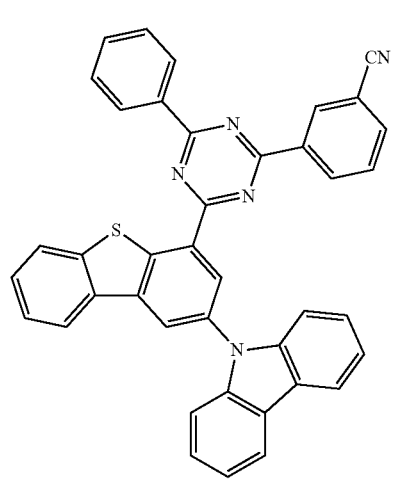
GH6
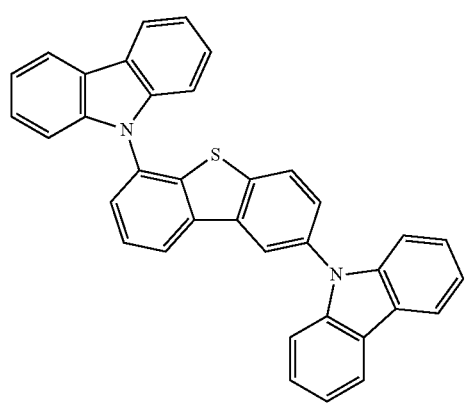
GH7

A current was applied to each of the organic light emitting devices manufactured in Examples 1-1 to 1-7 and Comparative Examples 1-1 to 1-6, and results of the following Table 1 were obtained. In Table 1, the color coordinate means a CIE color coordinate measured under current density of 10 mA/cm$^2$.

TABLE 1

| Category | Compound | Voltage (V@10 mA/cm$^2$) | Efficiency (cd/A@10 mA/cm$^2$) | Color Coordinate (x, y) |
| --- | --- | --- | --- | --- |
| Example 1-1 | 1 | 4.1 | 20 | (0.32, 0.64) |
| Example 1-2 | 2 | 4.0 | 21 | (0.32, 0.63) |
| Example 1-3 | 3 | 4.0 | 22 | (0.33, 0.63) |
| Example 1-4 | 4 | 3.9 | 21 | (0.32, 0.64) |
| Example 1-5 | 5 | 4.0 | 20 | (0.32, 0.63) |
| Example 1-6 | 6 | 4.0 | 21 | (0.33, 0.63) |
| Example 1-7 | 7 | 3.9 | 22 | (0.32, 0.63) |
| Comparative Example 1-1 | GH2 | 4.8 | 13 | (0.34, 0.61) |
| Comparative Example 1-2 | GH3 | 4.7 | 14 | (0.35, 0.60) |
| Comparative Example 1-3 | GH4 | 4.7 | 13 | (0.34, 0.61) |
| Comparative Example 1-4 | GH5 | 4.8 | 12 | (0.34, 0.62) |
| Comparative Example 1-5 | GH6 | 4.8 | 13 | (0.35, 0.61) |
| Comparative Example 1-6 | GH7 | 4.6 | 15 | (0.33, 0.62) |

As shown in Table 1, the devices of Examples 1-1 to 1-7 using the compound of Chemical Formula 1 all had decreased voltage and enhanced efficiency compared to the devices of the comparative examples.

It was identified that the compound of Chemical Formula 1 according to the present disclosure had an excellent ability of transferring electrons and holes to a dopant, and was usable in a delayed fluorescent organic light emitting device.

Example 2-1

An organic light emitting device was manufactured by forming a light emitting layer with a first host; a second host that is the compound of Chemical Formula 1 according to one embodiment of the present specification; and Compound GD-1 having phosphorescent properties.

A glass substrate on which indium tin oxide (ITO) was coated as a thin film to a thickness of 130 nm was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was formed by thermal vacuum depositing Compound HAT-CN to a thickness of 5 nm. On the hole injection layer, a first hole transfer layer was formed by thermal vacuum depositing Compound NPB to a thickness of 80 nm, and a second hole transfer layer was consecutively formed by vacuum depositing Compound HT-3 to a thickness of 50 nm.

Subsequently, a light emitting layer having a thickness of 40 nm was formed on the second hole transfer layer by vacuum depositing Compound GH-1, Compound 1, and Compound GD-1 that is a phosphorescent dopant in a weight ratio of 47.5:47.5:5.

A hole blocking layer was formed on the light emitting layer by vacuum depositing Compound ET-3 to a thickness of 5 nm, and an electron injection and transfer layer having a thickness of 25 nm was formed on the hole blocking layer by vacuum depositing Compound ET-4 and LiQ in a weight ratio of 1:1. On the electron transfer layer, a cathode was formed by consecutively depositing lithium fluoride (LiF) to a thickness of 1 nm and aluminum to a thickness of 100 nm thereon.

In the above-mentioned process, the deposition rates of the organic materials were maintained at 0.04 nm/sec to 0.07 nm/sec, the deposition rate of the lithium fluoride was maintained at 0.03 Å/sec, the deposition rate of the aluminum was maintained at 0.2 nm/sec, and the degree of vacuum during the deposition was maintained at $1\times10^{-7}$ torr to $5\times10^{-8}$ torr.

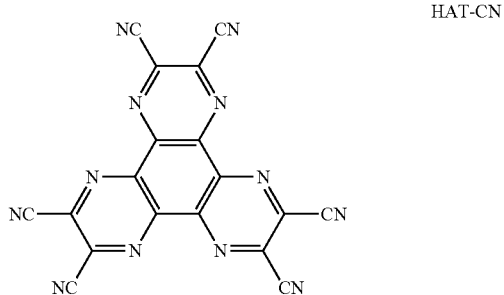

HAT-CN

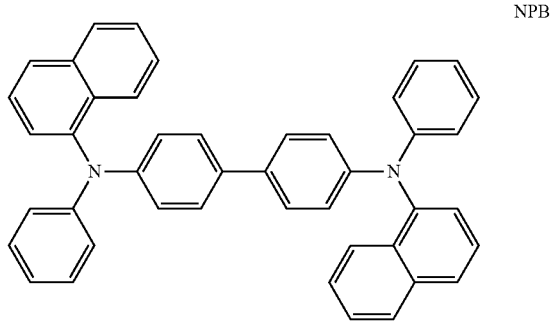

NPB

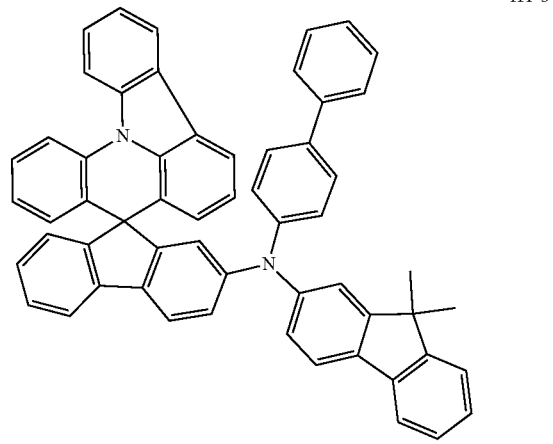

HT-3

GD-1

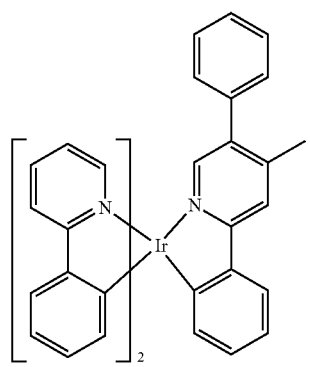

ET-4

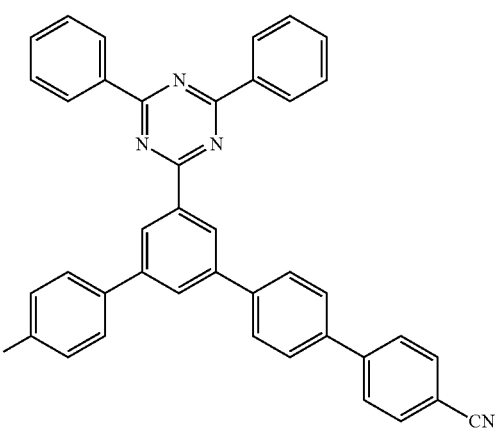

ET-3

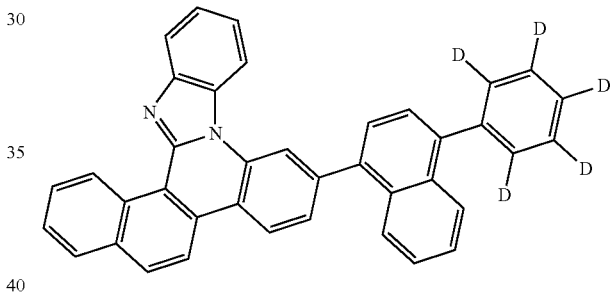

GH-1

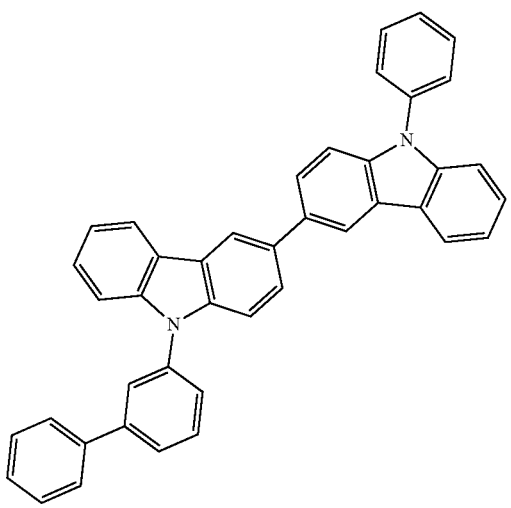

LiQ

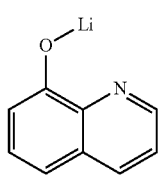

Examples 2-2 to 2-7

Organic light emitting devices were manufactured in the same manner as in Example 2-1 except that compounds of the following Table 2 were used instead of Compound 1.

Comparative Examples 2-1 to 2-6

Organic light emitting devices were manufactured in the same manner as in Example 2-1 except that the following Compounds GH2 to GH7 were used instead of Compound 1.

GH2
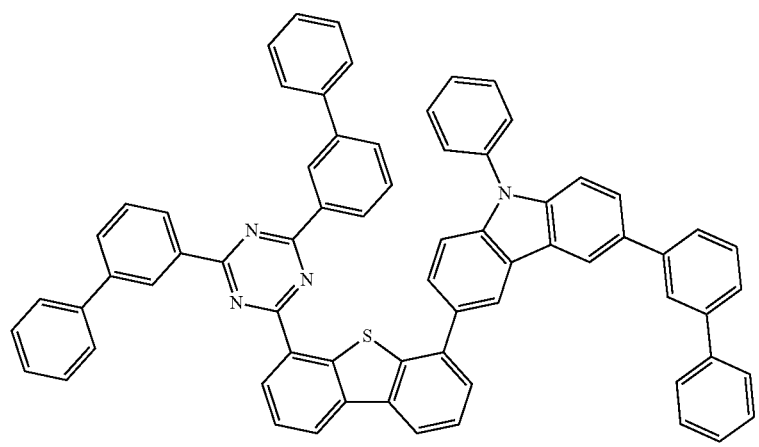
GH3
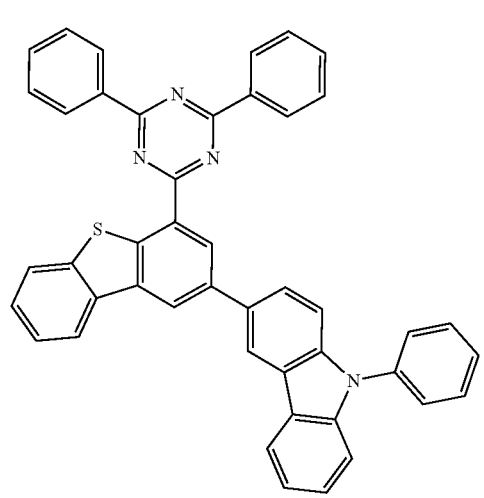
GH4
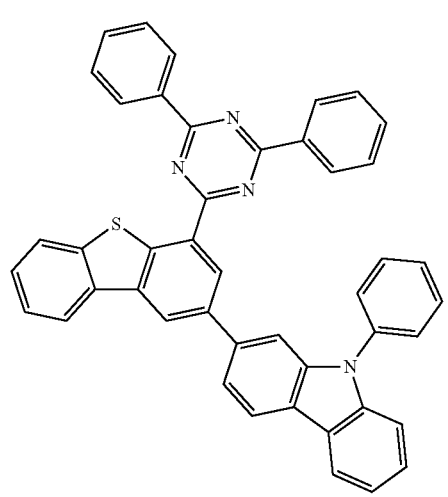

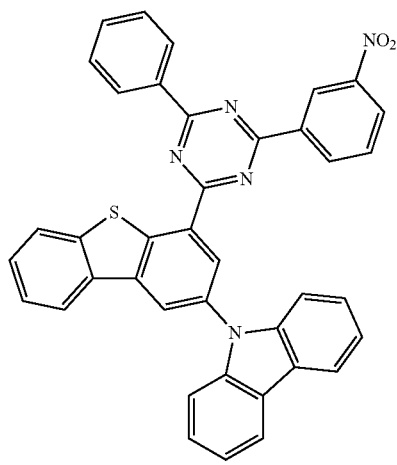
GH5
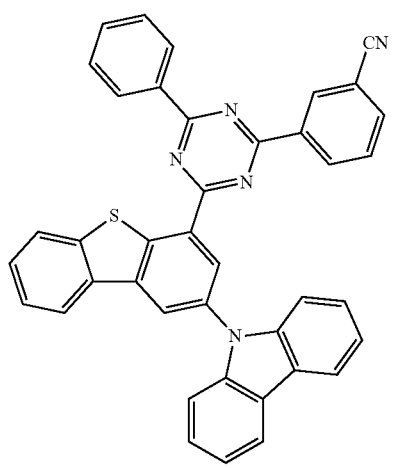
GH6
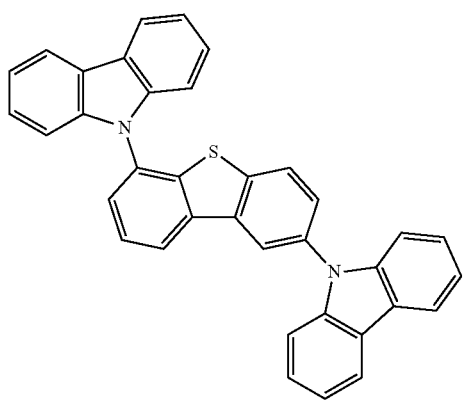
GH7

A current was applied to each of the organic light emitting devices manufactured in Examples 2-1 to 2-7 and Comparative Examples 2-1 to 2-6, and results of the following Table 2 were obtained. In Table 2, the color coordinate means a CIE color coordinate measured under current density of 10 mA/cm$^2$.

TABLE 2

| Category | Compound (Light Emitting Layer) | Voltage (V@10 mA/cm$^2$) | Efficiency (cd/A@10 mA/cm$^2$) | Color Coordinate (x, y) |
|---|---|---|---|---|
| Example 2-1 | 1 | 3.8 | 22 | (0.29, 0.65) |
| Example 2-2 | 2 | 3.9 | 22 | (0.28, 0.66) |
| Example 2-3 | 3 | 3.9 | 23 | (0.29, 0.65) |
| Example 2-4 | 4 | 3.8 | 22 | (0.29, 0.66) |
| Example 2-5 | 5 | 3.9 | 21 | (0.28, 0.66) |
| Example 2-6 | 6 | 3.8 | 22 | (0.29, 0.65) |
| Example 2-7 | 7 | 3.8 | 21 | (0.29, 0.66) |
| Comparative Example 2-1 | GH2 | 4.5 | 11 | (0.32, 0.63) |
| Comparative Example 2-2 | GH3 | 4.4 | 15 | (0.33, 0.62) |
| Comparative Example 2-3 | GH4 | 4.4 | 15 | (0.32, 0.63) |
| Comparative Example 2-4 | GH5 | 4.4 | 16 | (0.33, 0.63) |
| Comparative Example 2-5 | GH6 | 4.5 | 15 | (0.32, 0.62) |
| Comparative Example 2-6 | GH7 | 4.6 | 8 | (0.31, 0.63) |

As shown in Table 2, the devices of Examples 2-1 to 2-7 using the compound of Chemical Formula 1 all had decreased voltage and enhanced efficiency compared to the devices of the comparative examples.

It was identified that the compound of Chemical Formula 1 according to the present disclosure had an excellent ability of transferring electrons and holes to a dopant, and was usable in a green phosphorescent organic light emitting device.

Hereinbefore, preferred embodiments of the present disclosure have been described, however, the present disclosure is not limited thereto, and various modifications may be made within the scope of the claims and the detailed descriptions of the disclosure, and these also fall within the category of the disclosure.

What is claimed is:

1. A compound of the following Chemical Formula 2:

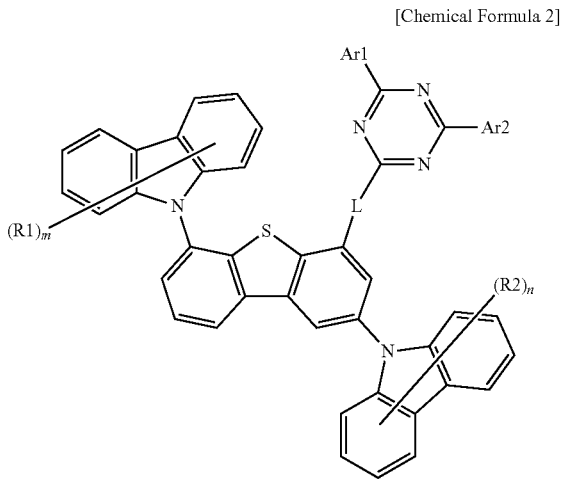

[Chemical Formula 2]

wherein, in Chemical Formula 2:

L is a direct bond or a substituted or unsubstituted arylene group;

Ar1 and Ar2 are the same as or different from each other, and each independently a substituted or unsubstituted aryl group; a substituted or unsubstituted heterocyclic group; or a substituted or unsubstituted silyl group, R1 and R2 are the same as or different from each other, and each independently hydrogen, deuterium, a halogen group, a nitrile group, a nitro group, a substituted or unsubstituted alkyl group, a substituted or unsubstituted cycloalkyl group, a substituted or unsubstituted alkoxy group, a substituted or unsubstituted arylsilyl group, a substituted or unsubstituted alkylsilyl group, a substituted or unsubstituted aryl group, or a substituted or unsubstituted heterocyclic group;

m and n are each an integer of 0 to 8;

when m is 2 or greater, R1s are the same as or different from each other; and when n is 2 or greater, R2s are the same as or different from each other.

2. The compound of claim 1, wherein L is a direct bond; or a substituted or unsubstituted phenylene group.

3. The compound of claim 1, wherein Ar1 and Ar2 are the same as or different from each other, and each independently a substituted or unsubstituted phenyl group; a substituted or unsubstituted biphenyl group; a substituted or unsubstituted dibenzothiophene group; a substituted or unsubstituted dibenzofuran group; or a substituted or unsubstituted benzothiazole group.

4. The compound of claim 1, wherein the compound of Chemical Formula 2 is selected from among the following structural formulae:

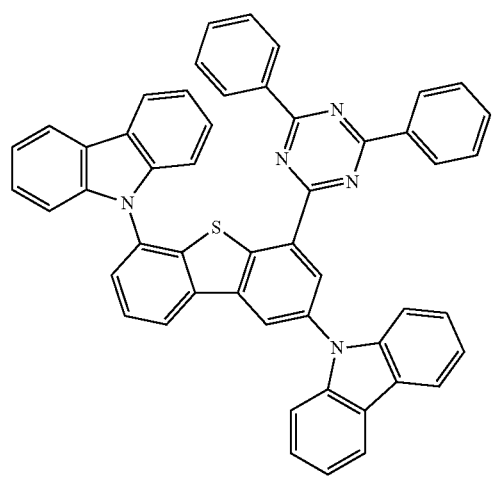
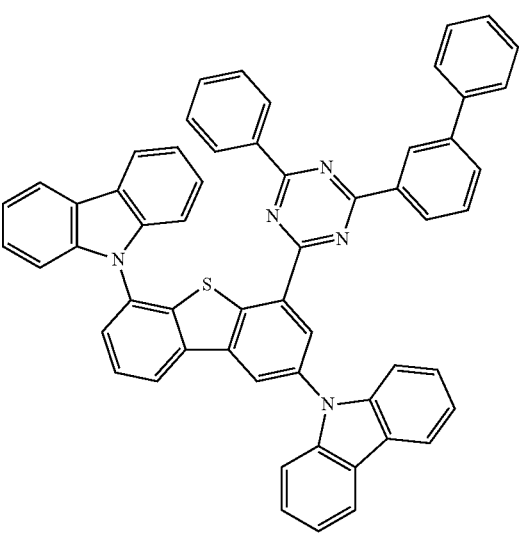
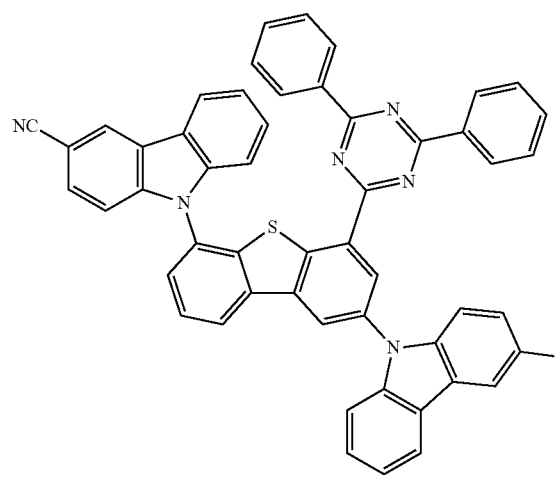
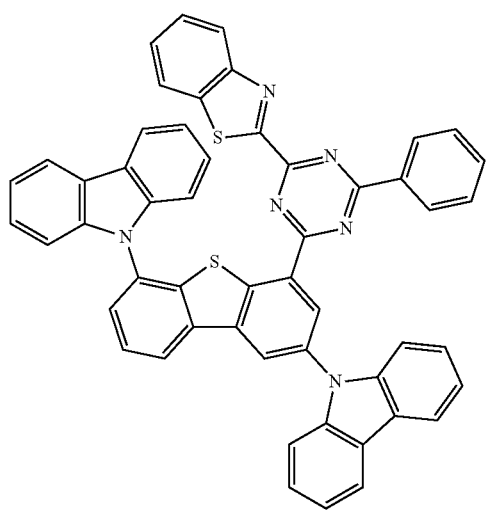
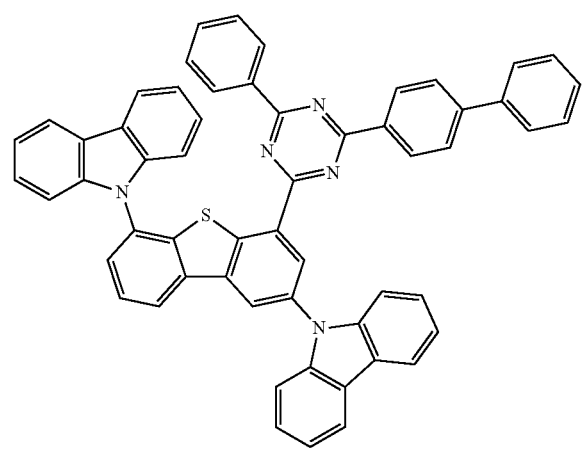
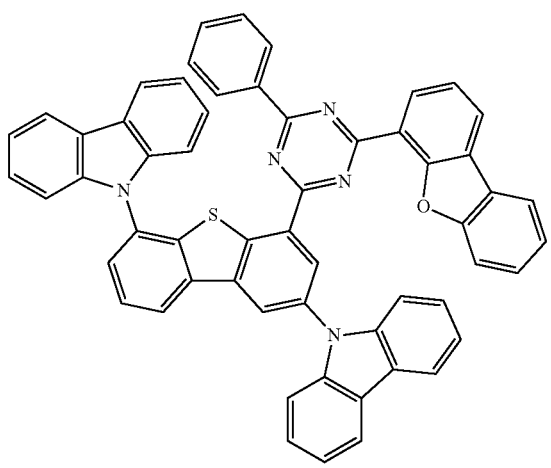

47
-continued
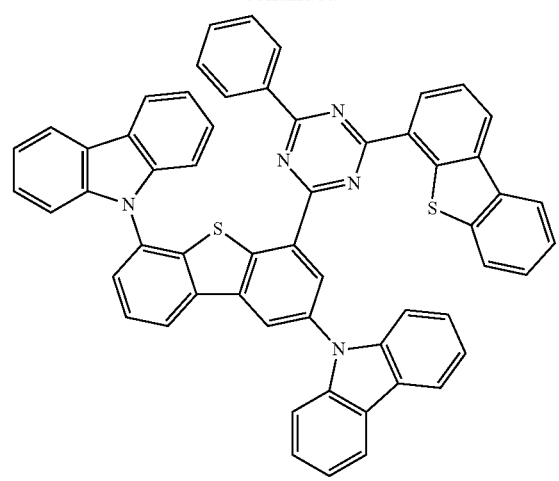
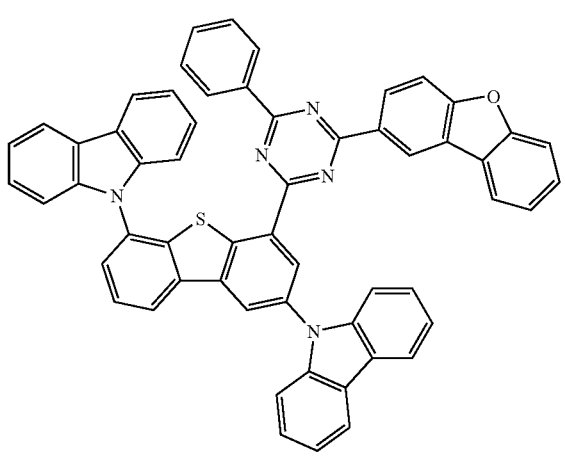
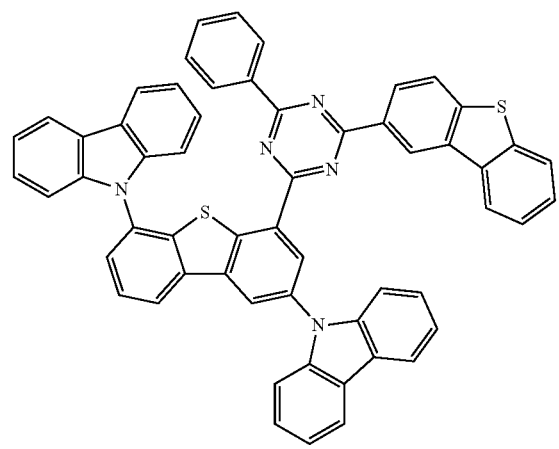
48
-continued
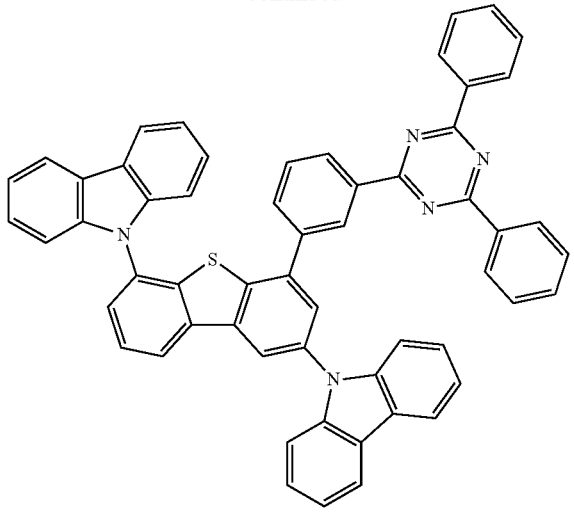
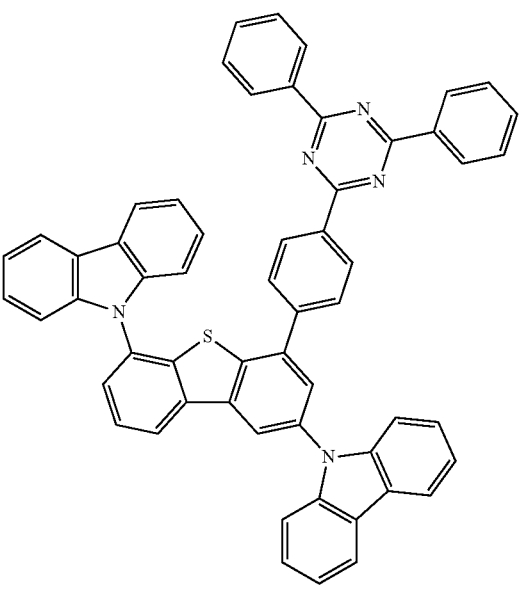
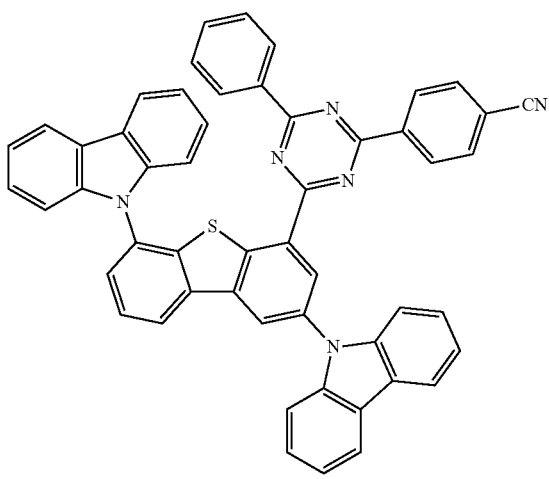

-continued

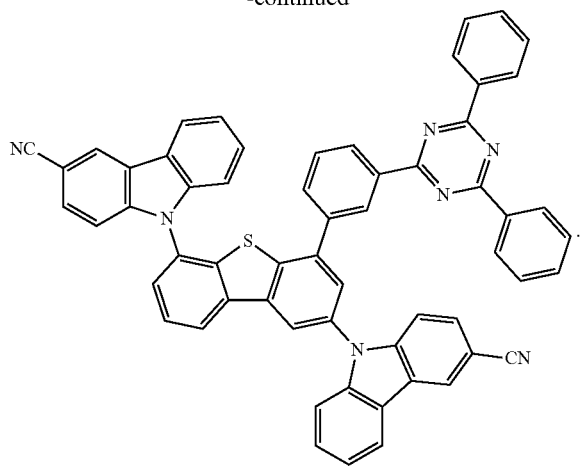

5. The compound of claim 1, wherein the compound of Chemical Formula 2 has a glass transition temperature of 120° C. or higher.

6. An organic light emitting device comprising:
a first electrode;
a second electrode provided opposite to the first electrode; and
one or more organic material layers provided between the first electrode and the second electrode,
wherein at least one the organic material layers includes the compound of claim 1.

7. The organic light emitting device of claim 6, wherein the organic material layer includes a light emitting layer, and the light emitting layer includes the compound of Chemical Formula 2.

8. The organic light emitting device of claim 6, wherein the organic material layer includes a light emitting layer, and the light emitting layer includes the compound of Chemical Formula 2 as a host.

9. The organic light emitting device of claim 6, wherein the organic material layer includes an electron injection layer, an electron transfer layer, or an electron injection and transfer layer, and the electron injection layer, the electron transfer layer, or the electron injection and transfer layer includes the compound of Chemical Formula 2.

10. The organic light emitting device of claim 6, wherein the organic material layer includes a hole injection layer, a hole transfer layer, or a hole injection and transfer layer, and the hole injection layer, the hole transfer layer, or the hole injection and transfer layer includes the compound of Chemical Formula 2.

* * * * *